US010687786B2

(12) United States Patent
Yamamoto

(10) Patent No.: US 10,687,786 B2
(45) Date of Patent: Jun. 23, 2020

(54) ULTRASOUND INSPECTION APPARATUS, ULTRASOUND INSPECTION METHOD AND RECORDING MEDIUM

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 700 days.

(21) Appl. No.: 14/671,236

(22) Filed: Mar. 27, 2015

(65) Prior Publication Data

US 2015/0196274 A1 Jul. 16, 2015

Related U.S. Application Data

(63) Continuation of application No. PCT/JP2013/075666, filed on Sep. 24, 2013.

(30) Foreign Application Priority Data

Sep. 28, 2012 (JP) .................................. 2012-215721
Jun. 14, 2013 (JP) .................................. 2013-125337

(51) Int. Cl.
*A61B 8/14* (2006.01)
*G01S 15/89* (2006.01)
(Continued)

(52) U.S. Cl.
CPC ............ *A61B 8/145* (2013.01); *A61B 8/4444* (2013.01); *A61B 8/4483* (2013.01); *A61B 8/485* (2013.01);
(Continued)

(58) Field of Classification Search
CPC ... A61B 8/5261; A61B 8/4245; A61B 8/0825; A61B 8/4416; A61B 8/485; A61B 8/58;
(Continued)

(56) References Cited

U.S. PATENT DOCUMENTS 4,893,284 A * 1/1990 Magrane ............... G01S 7/5205
367/12
2009/0326377 A1 12/2009 Hirama
(Continued)

FOREIGN PATENT DOCUMENTS

JP 05-095946 A * 4/1993 ............... A61B 8/00
JP 2009-90102 A 4/2009
(Continued)

OTHER PUBLICATIONS

Hennnnsen et al. Ultrasound in Med. & Biol. 38:708-716 (Year: 2012).*

(Continued)

*Primary Examiner* — Jeffrey G Hoekstra
*Assistant Examiner* — Patrick M Mehl
(74) *Attorney, Agent, or Firm* — Birch, Stewart, Kolasch & Birch, LLP

(57) ABSTRACT

An ultrasound inspection apparatus of the present invention includes: a probe provided with a plurality of elements; a transmitter configured to transmit the ultrasonic beam to an inspection object using the probe; a receiver configured to receive an ultrasonic echo signal from the inspection object; a sound velocity determiner configured to determine a sound velocity value inside the inspection object; and an element data processing section configured to generate a piece of second element data from at least two pieces of first element data using the sound velocity value, the piece of second element data corresponding to any of the at least two pieces of first element data, the sound velocity determiner being configured to obtain an optimum sound velocity value by optimizing the sound velocity value which is used when the piece of second element data is created in the element data processing section.

13 Claims, 9 Drawing Sheets

(51) Int. Cl.
*A61B 8/00* (2006.01)
*G01S 15/02* (2006.01)
*A61B 8/08* (2006.01)
*G01S 7/52* (2006.01)

(52) U.S. Cl.
CPC .......... *A61B 8/5207* (2013.01); *A61B 8/5223* (2013.01); *A61B 8/5269* (2013.01); *G01S 7/52036* (2013.01); *G01S 7/52049* (2013.01); *G01S 7/52085* (2013.01); *G01S 15/02* (2013.01); *G01S 15/8915* (2013.01); *G01S 15/8997* (2013.01); *A61B 8/4488* (2013.01)

(58) Field of Classification Search
CPC ............. G01S 7/52049; G01S 15/8915; G01S 15/8997; G10K 11/346
See application file for complete search history.

(56) References Cited

U.S. PATENT DOCUMENTS

| | | | | |
|---|---|---|---|---|
| 2010/0076312 | A1* | 3/2010 | Katsuyama | ............... A61B 8/00 600/443 |
| 2010/0331692 | A1* | 12/2010 | Kakee | ..................... A61B 8/06 600/443 |
| 2011/0077518 | A1* | 3/2011 | Miyachi | ............. A61B 5/02007 600/443 |

FOREIGN PATENT DOCUMENTS

| | | | | |
|---|---|---|---|---|
| JP | 2009-90103 | A | | 4/2009 |
| JP | 2009-90104 | A | | 4/2009 |
| JP | 2009-240700 | A | | 10/2009 |
| JP | 2010-082190 | A * | 4/2010 | ............... A61B 8/00 |
| JP | 2010-82190 | A | | 4/2010 |

OTHER PUBLICATIONS

English translation of the International Preliminary Report on Patentability and Written Opinion of the International Searching Authority (Forms PCT/IB/338, PCT/IB/373 and PCT/ISA/237), dated Apr. 9, 2015, for International Application No. PCT/JP2013/075666.

International Search Report, issued in PCT/JP2013/075666, dated Oct. 29, 2013.

Japanese Office Action and partial English translation dated Oct. 13, 2015 for corresponding Application No. 2013-125337.

* cited by examiner

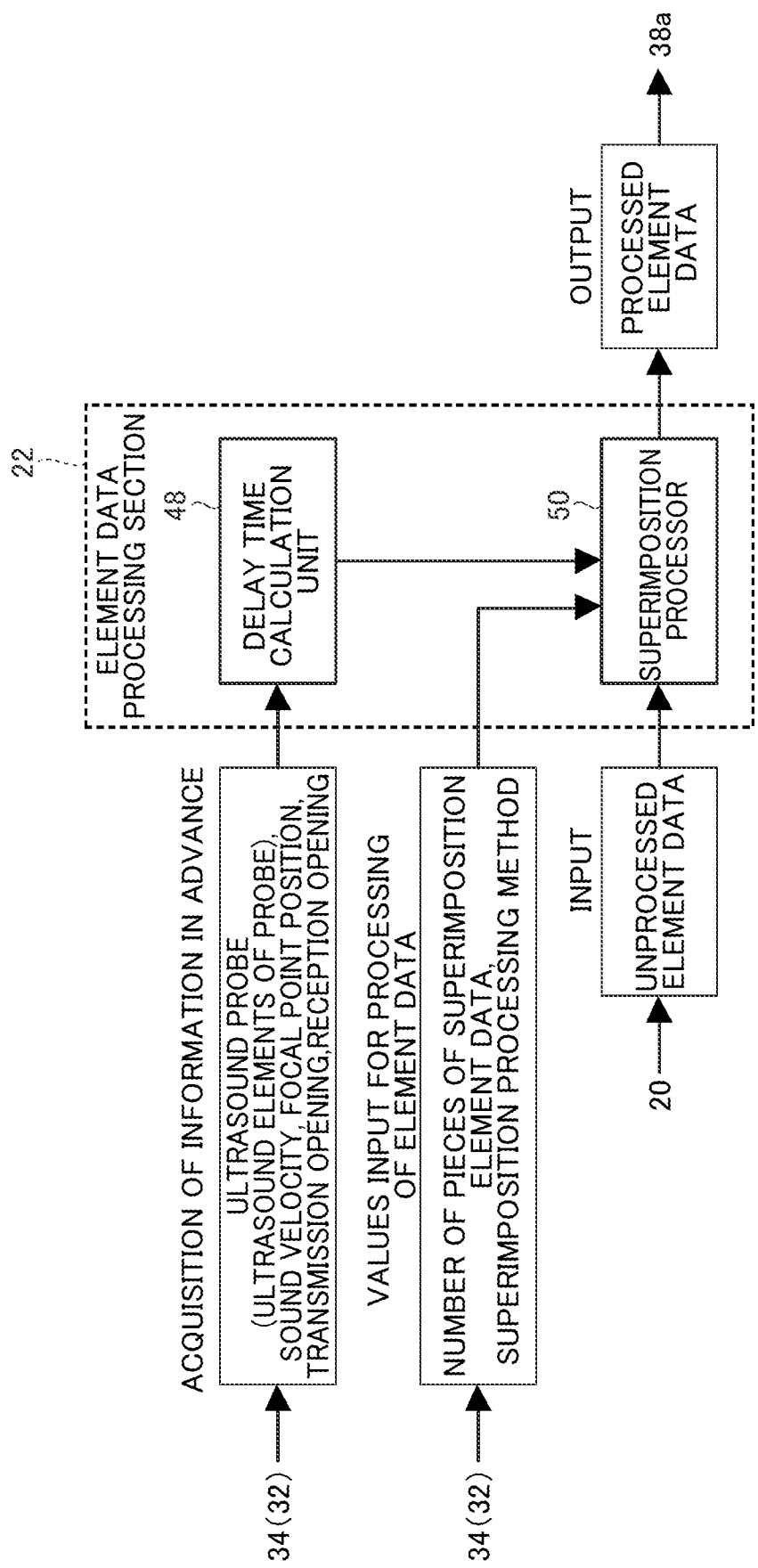

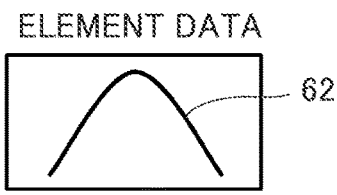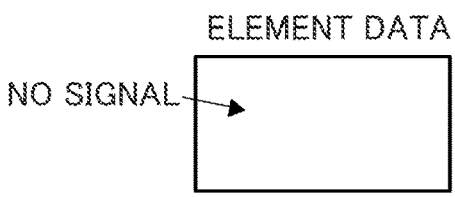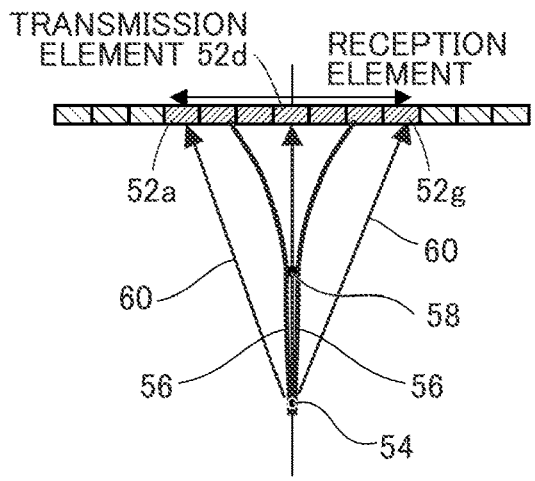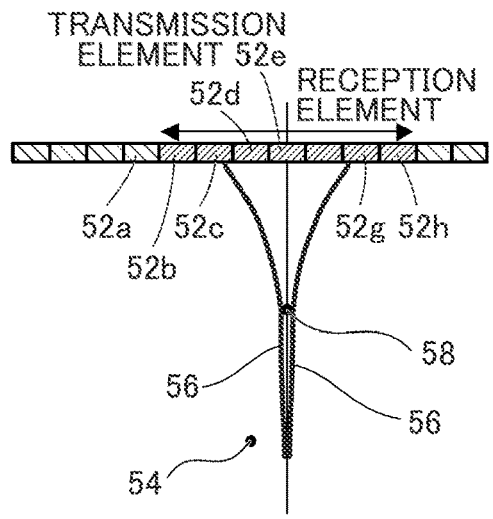
FIG. 4B
FIG. 4D
FIG. 4A
FIG. 4C
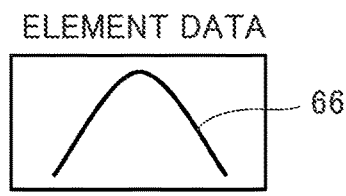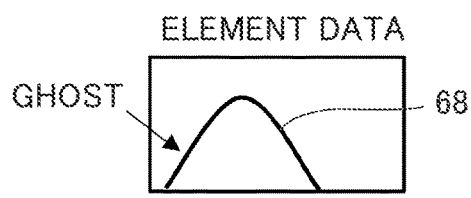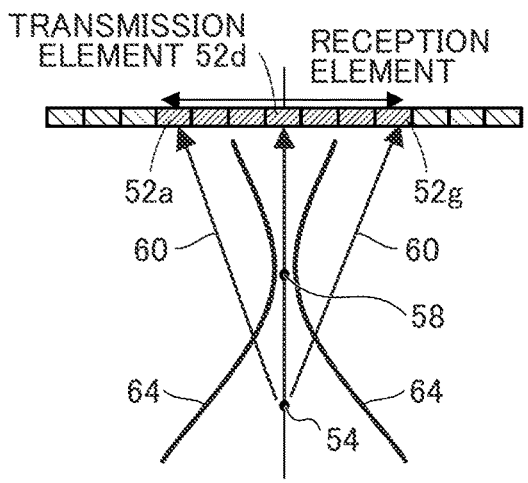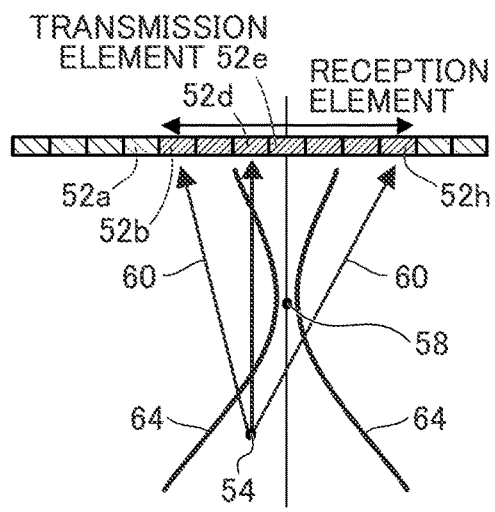
FIG. 5B
FIG. 5D
FIG. 5A
FIG. 5C

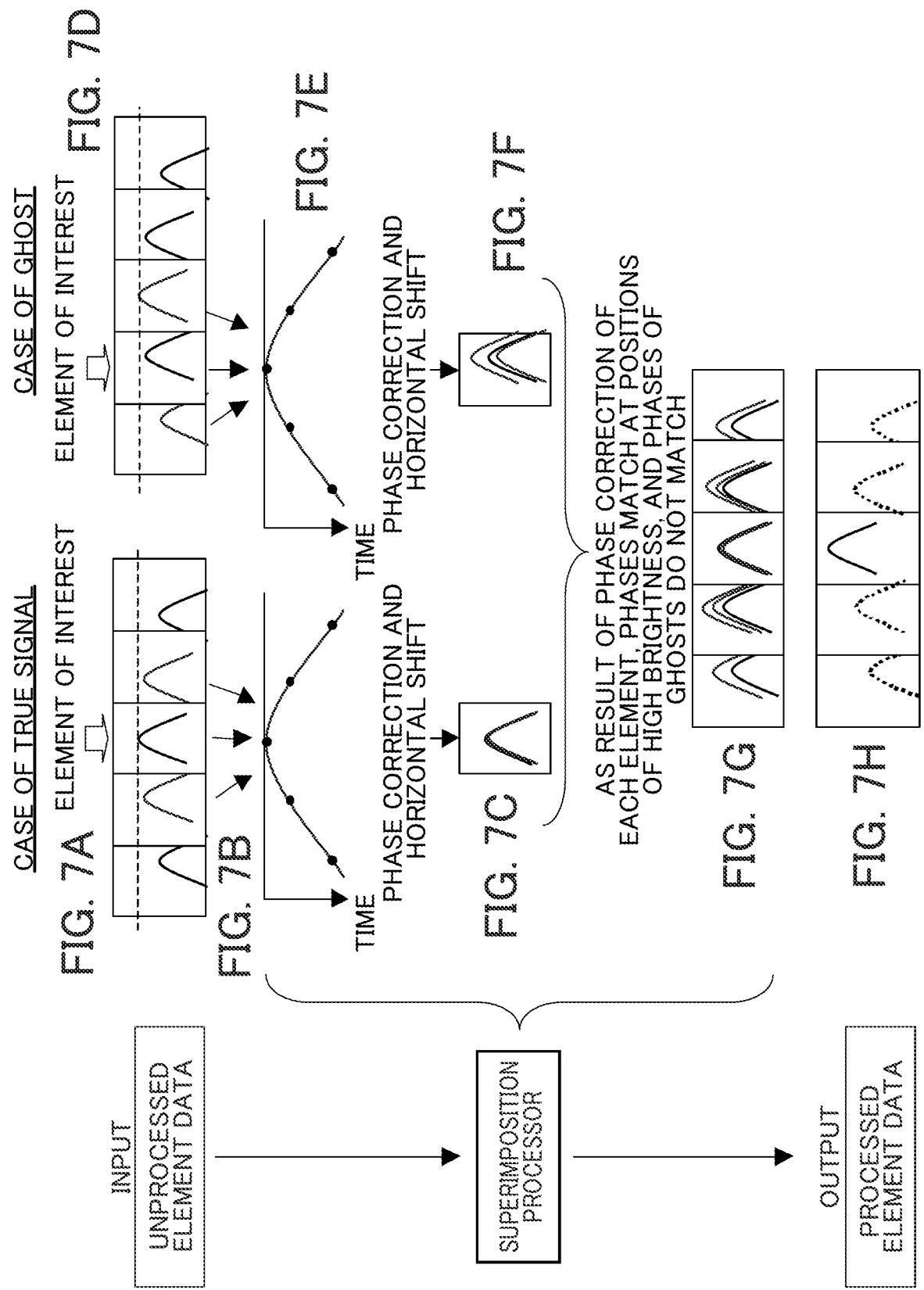

ULTRASOUND INSPECTION APPARATUS, ULTRASOUND INSPECTION METHOD AND RECORDING MEDIUM

CROSS-REFERENCE TO RELATED APPLICATIONS

This application is a Continuation of PCT international Application No. PCT/JP2013/075666 filed on Sep. 24, 2013, which claims priority under 35 U.S.C. § 119(a) to Japanese Patent Application No. 2012-215721 filed on Sep. 28, 2012 and Japanese Patent Application No. 2013-125337 filed on Jun. 14, 2013. Each of the above application(s) is hereby expressly incorporated by reference, in its entirety, into the present application.

BACKGROUND OF THE INVENTION

The present invention relates to an ultrasound inspection apparatus that generates an ultrasound image to be used in the inspection and diagnosis of an inspection object by capturing an image of the inspection object such as an organ inside a living body by transmitting and receiving an ultrasonic beam, and relates to an ultrasound inspection method and a recording medium.

Conventionally in the medical field, ultrasound inspection apparatuses such as ultrasound image diagnostic apparatuses that utilize ultrasound images have been put to practical use. In general, such an ultrasound inspection apparatus includes an ultrasound probe having a plurality of elements (ultrasound transducers) built therein and an apparatus main body connected to this ultrasound probe. The ultrasound inspection apparatus generates an ultrasound image by transmitting ultrasonic beams toward an inspection object (subject) from the plurality of elements of the ultrasound probe, receiving ultrasonic echoes from the subject with the ultrasound probe and then electrically processing the received ultrasonic echo signals in the apparatus main body.

When an ultrasound image is generated in such an ultrasound inspection apparatus, ultrasonic beams are focused and transmitted from the plurality of elements of the probe onto an inspection region of the subject such as an organ inside a living body or a lesion inside that organ, and ultrasonic echoes from reflectors of the inspection region such as the surfaces and boundaries of the organ or lesion are received via the plurality of elements. However, because ultrasonic echoes reflected by the same reflector are received by a plurality of elements, compared to an ultrasonic echo signal that is reflected by a reflector positioned at the focal position of an ultrasonic beam transmitted from a transmission element and received by the transmission element, an ultrasonic echo signal that is reflected by the same reflector and received by another element different to the transmission element is delayed. Consequently, in an ultrasound inspection apparatus, ultrasonic echo signals received by the plurality of elements are subjected to analog-to-digital (A/D) conversion to form a piece of element data, and then the piece of element data is subjected to reception focus processing, that is, the piece of element data is subjected to delay correction to match the phase of the element data and to phasing addition to generate sound ray signals, and then an ultrasound image is generated on the basis of the thus-obtained sound ray signals.

In such an ultrasound inspection technology, in order to improve the image quality of an ultrasound image, signals obtained by transmitting a plurality of ultrasonic beams that converge at a plurality of different focal points have been added together and as a result the quality of signals has been improved from the past.

For example, JP 2009-240700 A discloses an ultrasound diagnostic apparatus in which a virtual point sound source is formed by causing transmission ultrasonic waves emitted from a plurality of transducer elements that make up a transmission transducer element group to converge at a transmission convergence point, and then reception ultrasound waves reflected from a plurality of continuous observation points as a result of the transmission ultrasonic waves emitted from this point sound source are received by a plurality of transducer elements that make up a reception transducer element group, and reception phasing addition is performed on obtained reception signals for the number of channels such that an observation point becomes a reception convergence point. In addition, in this ultrasound diagnostic apparatus, the same reception phasing addition is also performed on reception signals obtained using the reception transducer element group and each transmission transducer element group sequentially shifted in the direction of the array of the transducer elements, and transmission phasing addition is performed on the post-reception phasing addition reception signals to correct a transmission delay caused by the difference in propagation distance from each transmission convergence point to the observation point.

In the ultrasound diagnostic apparatus disclosed in JP 2009-240700 A, reception phasing addition and transmission phasing addition are performed on reception signals obtained from a plurality of transducer elements, and as a result, a transmission beam and a reception beam having a substantially uniformly fine beam width with respect to a depth direction of the subject can be formed with high precision and high sensitivity. Thus, JP 2009-240700 A discloses an ultrasound diagnostic apparatus that can generate and display image data that is excellent in terms of spatial resolution, contrast resolution and an S/N ratio (signal-noise ratio).

In particular, in JP 2009-240700 A (refer to the working example illustrated in FIG. 5 therein), as illustrated in FIG. 8, it is indicated that when the focuses of three transmission transducer element groups are converged at respective transmission convergence points (hereinafter, referred to as focal points) Ft1 to Ft3 and each focal point is regarded as a virtual point sound source (hereinafter, referred to as a virtual point sound source), reflection waves obtained as a result of wave fronts from each virtual point sound source being reflected at the position of the same observation point (reflection point) Px are received by the reception transducer element group. In JP 2009-240700 A, it is thereby assumed that signal quality can be improved from the past by adding together signals transmitted through a plurality of different focal points with respect to one point.

SUMMARY OF THE INVENTION

However, there is a problem with the technology disclosed in JP 2009-240700 A in that although images having higher image quality are obtained compared with the related art, it is necessary to generate a plurality of transmission beams by changing a transmission position in order to generate one line of data, the frame rate is reduced due to the number of times transmission is performed increasing compared with the related art, and the real-time characteristic deteriorates.

In addition, there is a problem with the technology disclosed in JP 2009-240700 A in that when there are variations in the distribution of sound velocity inside living body tissues, a shift is generated in the wave front from each virtual point sound source, and therefore precision deteriorates.

In order to solve the aforementioned problems of the related art, an objective of the present invention is to provide an ultrasound inspection apparatus, an ultrasound inspection method and a recording medium, in which multiline processing is performed in which pieces of element data obtained by transmissions from two or more different elements are superimposed when transmitting ultrasonic beams from a plurality of elements of an ultrasound probe, whereby the effect caused by the broadening of a transmission ultrasonic beam can be decreased, the SN ratio and the resolution can be increased, and then sharp ultrasound images of an optimum spatial resolution can be obtained without using a wide beam transmission-dedicated ultrasound probe, with the frame rate unchanged from that of the related art and with a high resolution independent of the width of a transmission beam, and ultrasound images of high image quality can be obtained in which the effect of variations in sound velocity inside living body tissues is reduced by performing sound velocity correction with the calculation of the multiline processing included therein.

In the specification of Japanese Patent Application No. 2012-158009 relating to a prior application by the present applicant, the present inventor proposed an ultrasound inspection apparatus capable of obtaining ultrasound images of good image quality by performing multiline processing when transmitting and receiving ultrasonic beams from a plurality of elements of an ultrasound probe. Although a description is given regarding sound velocity correction in which variations in a sound velocity distribution are corrected in the technology disclosed in the prior application as a result of further diligent studies in order to achieve the aforementioned objective, the sound velocity is only corrected from the reflection point (observation point Px in FIG. 6 of the above-cited JP 2009-240700 A) up to the probe, and the sound velocity from the transmission elements, which form the virtual point sound sources, up to the reflection point (point Px) is not corrected, and therefore it has been found that the correction of sound velocity is insufficient, thereby reaching the present invention.

In other words, the present invention provides an ultrasound inspection apparatus configured to inspect an inspection object using an ultrasonic beam, the apparatus comprising:

a probe having a plurality of elements arrayed therein, the probe being configured to transmit the ultrasonic beam, receive an ultrasonic echo reflected by the inspection object, and output an analog element signal corresponding to the received ultrasonic echo;

a transmitter configured to cause, a plurality of times, the probe to transmit the ultrasonic beam in such a way as to form a predetermined transmission focus using the plurality of elements;

in accordance with transmission of each ultrasonic beam, a receiver configured to receive the analog element signal output from the plurality of elements and to perform predetermined processing on the analog element signal;

an AD converter configured to subject the analog element signal processed by the receiver to A/D conversion to produce a piece of first element data constituted by a digital element signal;

a sound velocity determiner configured to determine a sound velocity value inside the inspection object; and an element data processing section configured to generate a piece of second element data from at least two pieces of the first element data using the sound velocity value inside the inspection object, the piece of second element data corresponding to any of the at least two pieces of first element data, the sound velocity determiner being configured to obtain an optimum sound velocity value by optimizing the sound velocity value, the sound velocity value being used when the piece of second element data is created from the at least two pieces of first element data in the element data processing section.

In the ultrasound inspection apparatus, it is preferable that the sound velocity determiner includes the element data processing section and is configured to obtain an optimum sound velocity by optimizing the sound velocity value used in a delay time correction calculation for the at least two pieces of first element data in the element data processing section.

It is also preferable that the sound velocity determiner is configured to determine a sound velocity value of each of a plurality of regions, the plurality of regions being obtained by the inspection region being divided.

It is also preferable for the ultrasound inspection apparatus to further include an element data storage configured to retain some pieces of the first element data including the at least two pieces of first element data or all pieces of the first element data.

It is also preferable that the element data storage retains the at least two pieces of first element data including a piece of reception data, received for each piece of element data, for each reception time in each element, and the at least two pieces of first element data are generated as a result of the transmitter transmitting the ultrasonic beam for each of at least two overlapped target regions inside the inspection target region and the receiver receiving a signal of the ultrasonic echo generated for each of the at least two overlapped target regions inside the inspection region by the ultrasonic beam; and the element data processing section generates the piece of second element data from the at least two pieces of first element data, based on a geometrical arrangement of elements when the ultrasonic beam for each piece of element data is transmitted and a geometrical arrangement of the elements of the piece of reception data for each piece of element data.

It is also preferable that the transmitter transmits the ultrasonic beam a plurality of times while changing a central element.

It is also preferable that the element data processing section includes a delay time calculator configured to calculate a delay time of each of the at least two pieces of first element data using the sound velocity value inside the inspection object, and a superimposition processor configured to generate the piece of second element data by superimposing the at least two pieces of first element data based on each calculated delay time and a position of an element of the probe at which receiving has been carried out.

It is also preferable for the ultrasound inspection apparatus to further include an image generator configured to generate an ultrasound image based on the piece of second element data generated in the element data processing section, the element data processing section being configured to create one line of the piece of second element data on an ultrasound image to be generated by the image generator.

It is also preferable that the sound velocity determiner includes:

the element data processing section;

a sound velocity changing section configured to change the sound velocity value of the inspection object used in the delay time calculation in the element data processing section;

the element data processing section configured to create the piece of second element data using the sound velocity value changed by the sound velocity changing section;

a phasing addition section configured to generate a sound ray signal by subjecting the piece of second element data created by the element data processing section to phasing addition using the sound velocity value changed by the sound velocity changing section;

an image generator configured to generate an ultrasound image based on the sound ray signal generated in the phasing addition section;

an image quality index calculator configured to calculate an image quality index for the ultrasound image generated in the image generator;

a determiner configured to make a determination for the image quality index for the ultrasound image calculated in the image quality index calculator; and a sound velocity setting section configured to set the optimum sound velocity value in accordance with a determination result for the image quality index made by the determiner.

It is also preferable that the sound velocity determiner calculates a plurality of the image quality indices corresponding to all of a plurality of the respective sound velocity values changed by the sound velocity changing section, by repeatedly performing an operation in which, each time the sound velocity changing section changes the sound velocity value by a predetermined sound velocity interval from an initial sound velocity value to a final sound velocity value, the element data processing section creates the piece of second element data using the changed sound velocity value, the phasing addition section generates the sound ray signal by subjecting the piece of second element data to phasing addition using the same sound velocity value, the image generator creates the ultrasound image based on the sound ray signal, and the image quality index calculator calculates the image quality index for the ultrasound image; and the determiner determines an optimum image quality index from among the plurality of image quality indices calculated in the image quality index calculator for all of the plurality of respective sound velocity values, and the sound velocity setting section sets a sound velocity value corresponding to the optimum image quality index determined in the determiner as the optimum sound velocity value.

It is also preferable for the ultrasound inspection apparatus to further include a second sound velocity determiner upstream of the sound velocity determiner, the second sound velocity determiner being configured to calculate an optimum sound velocity value using the piece of first element data, the sound velocity determiner being configured to use the sound velocity value calculated by the second sound velocity determiner as an initial value.

In order to achieve the aforementioned object, the present invention further provides an ultrasound inspection method for inspecting an inspection object using a probe with a plurality of elements arrayed therein, the probe being configured to transmit an ultrasonic beam, to receive an ultrasonic echo reflected by the inspection object, and to output an analog element signal corresponding to the received ultrasonic echo, the method comprising:

a step of causing, a plurality of times, the probe to transmit an ultrasonic beam in such a way as to form a predetermined transmission focus using the plurality of elements, and causing the plurality of elements to output an analog element signal in accordance with transmission of each ultrasonic beam;

a step of subjecting the analog element signal to A/D conversion to produce a piece of first element data constituted by a digital element signal; and a step of determining, using a sound velocity value in the inspection object, an optimum sound velocity value by optimizing the sound velocity value used when creating, from at least two pieces of the first element data, a piece of second element data corresponding to any of the pieces of first element data.

In the ultrasound inspection method, it is preferable that, in the step of determining the optimum sound velocity value, a plurality of image quality indices corresponding to all of a plurality of the respective changed sound velocity values are calculated by repeatedly performing an operation in which, each time the sound velocity value is changed by a predetermined sound velocity interval from an initial sound velocity value to a final sound velocity value, the piece of second element data is created using the changed sound velocity value, a sound ray signal is generated by subjecting the piece of second element data to phasing addition using the same sound velocity value, the ultrasound image is created based on the generated sound ray signal, and the image quality index for the ultrasound image is calculated by the image quality index calculator, and an optimum image quality index is determined from among the plurality of image quality indices calculated for all of the plurality of respective sound velocity values, and a sound velocity value corresponding to the determined optimum image quality index is set as the optimum sound velocity value.

In order to achieve the aforementioned object, the present invention further provides a non-transitory computer-readable recording medium storing a program for causing a computer to execute:

in order to inspect an inspection object by transmitting an ultrasonic beam and receiving an ultrasonic echo reflected by the inspection object, a step of causing, a plurality of times, a probe with a plurality of elements arrayed therein to transmit an ultrasonic beam in such a way as to form a predetermined transmission focus using the plurality of elements, causing the plurality of elements to output an analog element signal in accordance with transmission of each ultrasonic beam, and causing the analog element signal to be subjected to A/D conversion to obtain a plurality of pieces of first element data constituted by digital element signals; and a step of determining, using a sound velocity value inside the inspection object, an optimum sound velocity value by optimizing the sound velocity value used when creating, from at least two pieces of the obtained first element data, a piece of second element data corresponding to any of the pieces of first element data.

According to the present invention, multiline processing is performed in which pieces of element data obtained by transmissions from two or more different elements are superimposed when transmitting ultrasonic beams from a plurality of elements of an ultrasound probe, whereby the effect caused by the broadening of a transmission ultrasonic beam can be decreased, the SN ratio and the resolution can be increased, and then sharp ultrasound images of an optimum spatial resolution can be obtained without using a wide beam transmission-dedicated ultrasound probe, with the frame rate unchanged from that of the related art and with a high resolution independent of the width of a transmission beam, and ultrasound images of high image quality can be obtained in which the effect of variations in sound velocity inside living body tissues is reduced by performing sound velocity correction with the calculation of the multiline processing included therein.

BRIEF DESCRIPTION OF THE DRAWINGS

FIG. 3 is a block diagram conceptually illustrating an example of a configuration of an element data processing section of the ultrasound inspection apparatus illustrated in FIG. 1.

FIGS. 4A and 4C are explanatory diagrams for the case where an ideal ultrasonic beam is transmitted from an element directly above a reflection point of a subject and the case where an ideal ultrasonic beam is transmitted from an element not directly above the reflection point of the subject, and FIGS. 4B and 4D are explanatory diagrams illustrating pieces of element data obtained in these cases.

FIGS. 5A and 5C are explanatory diagrams for the case where an actual ultrasonic beam is transmitted from an element directly above a reflection point of a subject and the case where an actual ultrasonic beam is transmitted from an element not directly above the reflection point of the subject, and FIGS. 5B and 5D are explanatory diagrams illustrating pieces of element data obtained in these cases.

FIGS. 7A, 7B and 70, and 7D, 7E and 7F are explanatory diagrams illustrating pieces of element data obtained by a plurality of elements in the cases of a true signal and a ghost, and illustrating the delay times and superimposed states of the pieces of element data, and FIGS. 7G and 7H are explanatory diagrams illustrating the superimposed states of the pieces of element data corresponding to a plurality of elements and the results therefor.

DETAILED DESCRIPTION OF THE INVENTION

An ultrasound inspection apparatus, an ultrasound inspection method and a recording medium will be described in detail hereinafter on the basis of preferred embodiments illustrated in the appended drawings.

Figure 1:
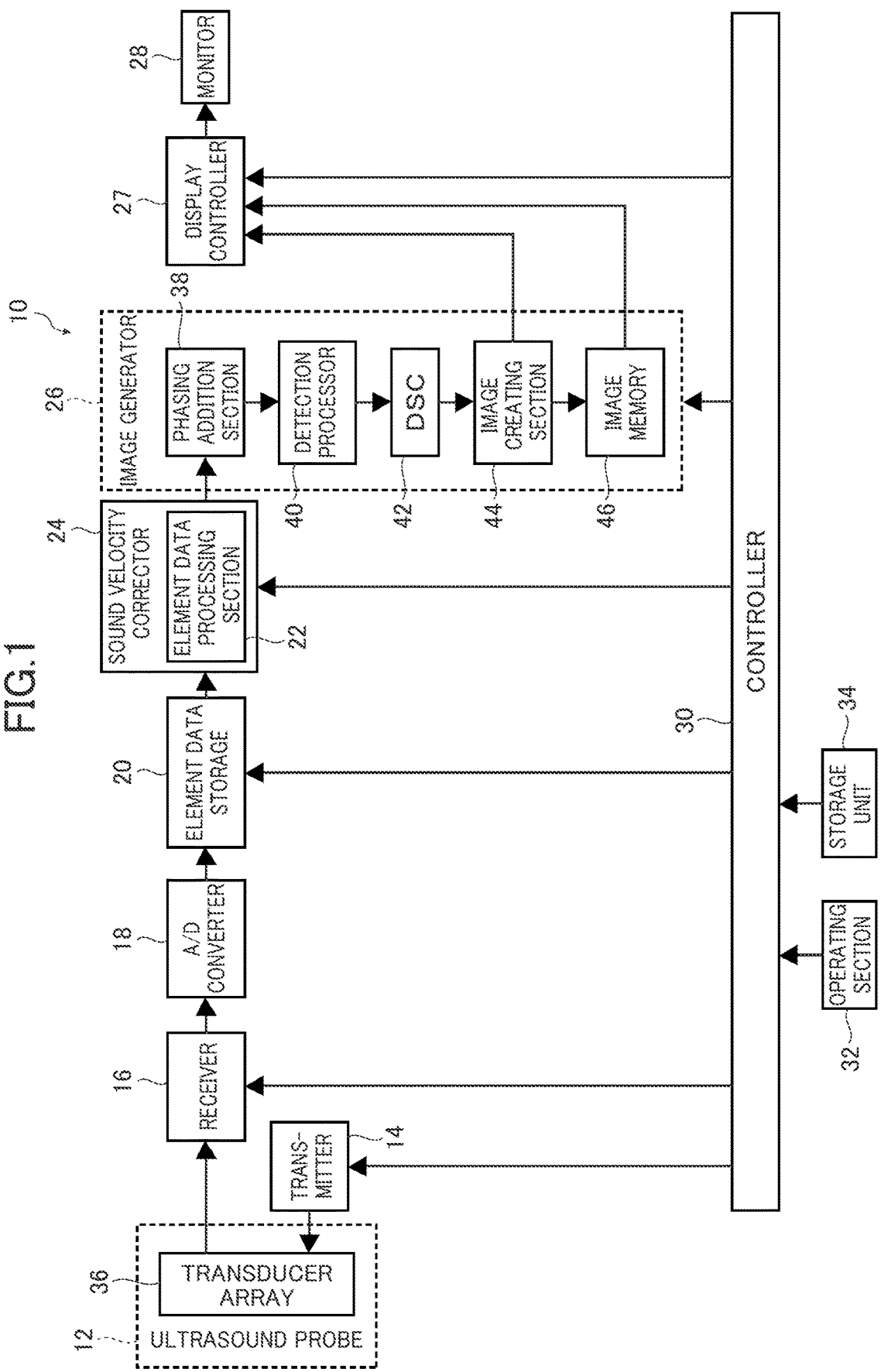
FIG. 1 is a block diagram conceptually illustrating an example of a configuration of an ultrasound inspection apparatus according to the present invention.

FIG. 1 is a block diagram conceptually illustrating a working example of a configuration of an ultrasound inspection apparatus of the present invention.

As illustrated in the figure, an ultrasound inspection apparatus 10 includes an ultrasound probe 12, a transmitter 14 and a receiver 16 connected to the ultrasound probe 12, an analog-to-digital (A/D) converter 18, an element data storage 20, a sound velocity corrector 24 provided with an element data processing section 22, an image generator 26, a display controller 27, a monitor 28, a controller 30, an operating section 32 and a storage unit 34.

The ultrasound probe 12 includes a transducer array 36 as used in a standard ultrasound inspection apparatus.

The transducer array 36 includes a plurality of elements, namely ultrasound transducers, arranged in a one-dimensional or two-dimensional array. When capturing an ultrasound image of an inspection object (hereinafter, referred to as a subject), the ultrasound transducers transmit ultrasonic beams to a subject in accordance with the respective driving signals supplied from the transmitter 14, receive ultrasonic echoes from the subject, and output reception signals. In the present embodiment, of the plurality of ultrasound transducers of the transducer array 36, each of a predetermined number of the ultrasound transducers that forms a group generates an individual component constituting a single ultrasonic beam. The group of the predetermined number of ultrasound transducers then generates the single ultrasonic beam to be transmitted to the subject.

Each ultrasound transducer is formed of an element, namely a transducer, in which electrodes are formed on both ends of a piezoelectric body composed of, for example, a piezoelectric ceramic such as lead zirconate titanate (PZT) or a macromolecular piezoelectric element such as polyvinylidene fluoride (PVDF) or a piezoelectric monocrystal such as a lead magnesium niobate-lead titanate solid solution (PMN-PT). In other words, the transducer array 36 can be referred to as a transducer array in which a plurality of transducers are arranged in a one-dimensional or two-dimensional array as a plurality of ultrasound elements.

When a pulse-shaped or continuous-wave-shaped voltage is applied to the electrodes of such transducers, the piezoelectric bodies expand and contract, pulse-shaped or continuous-wave-shaped ultrasonic waves are generated from the respective transducers, and an ultrasonic beam is formed by combining these ultrasonic waves. In addition, each transducer receives a propagating ultrasonic wave and as a result expands and contracts, thereby generating an electrical signal. These electrical signals are output as ultrasound reception signals.

The transmitter 14 includes, for example, a plurality of pulsers and, in order for ultrasonic beam components transmitted from a group of a predetermined number of ultrasound transducers (hereinafter, referred to as ultrasound elements) of the transducer array 36 to form a single ultrasonic beam, adjusts the delay amount of each driving signal and supplies such to the plurality of ultrasound elements that form the group, in accordance with a sound velocity or a sound velocity distribution that is set on the basis of a transmission delay pattern selected in accordance with a control signal from the controller 30.

The receiver 16 receives, from the subject, ultrasonic echoes generated by the interaction between the ultrasonic beam and the subject via the ultrasound elements of the transducer array 36, amplifies and outputs reception signals, namely an analog element signal for each ultrasound element, and supplies the amplified analog element signals to the A/D converter 18, in accordance with a control signal from the controller 30.

The A/D converter 18 is connected to the receiver 16 and converts the analog element signals supplied from the receiver 16 into pieces of digital element data. The A/D converter 18 supplies the pieces of A/D converted digital element data to the element data storage 20.

The element data storage 20 sequentially stores the pieces of digital element data output from the A/D converter 18. In addition, the element data storage 20 stores information relating to a frame rate that is input from the controller 30 (for example, parameters representing the depth of a reflection position of an ultrasonic wave, the density of scanning lines, and the visual field width), in association with the pieces of digital element data (hereinafter, referred to simply as element data).

When two or more target regions that are superimposed in a target region of positional coordinates of two or more dimensions are inspected in accordance with a control signal from the controller 30, the element data storage 20 stores and retains two or more pieces of element data generated for every two or more target regions from ultrasonic echoes received by the receiver 16 for two or more target regions, and the element data stored and retained in the element data storage 20 is two or more pieces of element data including a piece of reception data for each reception time in each element received for each piece of element data. In other words, the element data storage 20 stores some pieces of element data that includes two or more pieces of element data, or stores all pieces of first element data.

In addition, the element data processing section 22 is provided inside the sound velocity corrector 24 and performs multiline processing using a sound velocity (hereinafter, also referred to as an ambient sound velocity) of calculation coordinates of a predetermined calculation region inside the inspection region of the subject (a collection of sampling points or observation points inside a predetermined region) on the basis of control performed by the controller 30, that is, generates a piece of superimposition-processed element data (hereinafter, referred to as processed element data) by matching the reception times of and superimposing the two or more pieces of element data (hereinafter, referred to as unprocessed element data) generated for every two or more target regions stored and retained by the element data storage 20. It should be noted that, in the present invention, the sound velocity or ambient sound velocity of calculation coordinates refers to the average sound velocity in a transmission path where an ultrasonic beam transmitted from an ultrasound element of the transducer array 36 travels up to predetermined calculation coordinates inside the inspection region of the subject and in a reception path where an ultrasonic echo reflected at the calculation coordinates returns to the ultrasound element of the transducer array 36, that is, the average sound velocity between the ultrasound element of the transducer array 36 and the calculation coordinates.

The sound velocity corrector 24 is provided between the element data storage 20 and a phasing addition section 38 of the image generator 26 and is provided with the element data processing section 22 that performs multiline processing therein. The sound velocity corrector 24 obtains an optimum sound velocity for transmission/reception, namely the ambient sound velocity inside the inspection region of the subject, and therefore the most suitable ambient sound velocity for an ultrasound image of the inspection region of the subject, to be used by the phasing addition section 38, on the basis of the piece of processed data that has been subjected to multiline processing by the element data processing section 22, for calculation coordinates of the predetermined calculation region within the inspection region of the subject, on the basis of control performed by the controller 30. The sound velocity corrector 24 also obtains piece of processed data that has been subjected to multiline processing using the optimum ambient sound velocity by the element data processing section 22.

It should be noted that the element data processing section 22 and the sound velocity corrector 24 will be described in detail hereinafter.

The image generator 26 generates sound ray signals (reception data) from the piece of processed element data generated by the element data processing section 22 and supplied from the sound velocity corrector 24, and generates an ultrasound image from these sound ray signals, under the control of the controller 30.

The image generator 26 includes the phasing addition section 38, a detection processor 40, a digital scan converter (DSC) 42, an image creating section 44, and an image memory 46.

The phasing addition section 38 performs reception focus processing by adding respective delays to the pieces of processed element data generated by the element data processing section 22, in accordance with the reception direction set in the controller 30 and the optimum ambient sound velocity or distribution thereof obtained by the sound velocity corrector 24. A piece of reception data (sound ray signal) in which the focal points of ultrasonic echoes have been narrowed down is generated through this reception focus processing. It should be noted that in the case where the optimum ambient sound velocity or distribution thereof is not obtained in the sound velocity corrector 24, one reception delay pattern may be selected from among a plurality of reception delay patterns stored in advance, and an ambient sound velocity or distribution thereof set on the basis of the selected reception delay pattern may be used.

The phasing addition section 38 supplies the piece of reception data to the detection processor 40.

The detection processor 40 corrects attenuation due to distance in the piece of reception data generated by the phasing addition section 38, in accordance with the depth of the reflection position of an ultrasonic wave, and then performs envelope detection processing, whereby a piece of B-mode image data, which is tomographic image information regarding tissues inside the subject, is generated.

The DSC 42 converts (raster converts) the piece of B-mode image data generated by the detection processor 40 into a piece of image data conforming to a method for scanning typical television signals.

The image creating section 44 creates a piece of B-mode image data for inspection or display by subjecting the piece of B-mode image data input from the DSC 42 to various necessary image processing such as gradation processing, and then outputs the piece of created B-mode image data for inspection or display to a display controller 27 in order to display the piece of B-mode image data, or stores the piece of B-mode image data in the image memory 46.

The image memory 46 temporarily stores the piece of B-mode image data for inspection created by the image creating section 44. The piece of B-mode image data for inspection stored in the image memory 46 is read out by the display controller 27 in order to be displayed on the monitor 28 as needed.

The display controller 27 displays an ultrasound image on the monitor 28 on the basis of a B-mode image signal for inspection obtained by image processing being performed by the image creating section 44.

The monitor 28 includes a display device such as an LCD (Liquid Crystal Display) and displays the ultrasound image under the control of the display controller 27.

The controller 30 controls each part of the ultrasound inspection apparatus 10 on the basis of instructions input through the operating section 32 by an operator.

Here, when various types of information, in particular, information necessary in the calculation of the optimum ambient sound velocity used by the sound velocity corrector 24, information necessary in the calculation of a delay time used together with the optimum ambient sound velocity by the element data processing section 22 and the phasing addition section 38 of the image generator 26, and information necessary in the element data processing in the element data processing section 22, are input via the operating section 32 by an operator, and/or when the various types of information are read out from the storage unit 34, the controller 30 supplies the aforementioned various types of information input from the operating section 32 and/or read out from the storage unit 34, as needed to each part of the ultrasound inspection apparatus 10 such as the transmitter 14, the receiver 16, the element data storage 20, the element data processing section 22, the sound velocity corrector 24, the image generator 26 and the display controller 27.

The operating section 32 allows an operator to perform an input operation and can be formed of a keyboard, a mouse, a trackball, a touch panel, or the like.

In addition, the operating section 32 includes an input device allowing an operator to input various types of information as needed, such as, in particular, information relating to the plurality of ultrasound elements of the transducer array 36 of the probe 12, the inspection region of the subject, a calculation region therefor (calculation coordinates X1 to Xend), a sound velocity search range (initial sound velocity value Vst, final sound velocity value Vend, change amount of sound velocity value (sound velocity interval) $\Delta V$) for sound velocity correction (determination of optimum ambient sound velocity), a focal position of an ultrasonic beam, and transmission openings and reception openings of the transducer array 36 used in the calculation of the aforementioned delay time, and information relating to multiline processing of the piece of element data such as the number of pieces of superimposition element data and a superimposition processing method.

The storage unit 34 stores various types of information input from the operating section 32 such as, in particular, information relating to the aforementioned probe 12, calculation region, sound velocity search range, focal position, and transmission openings and reception openings, information relating to the multiline processing of element data such as the number of pieces of superimposition element data and the superimposition processing method, and information needed in the processing and operations of each part controlled by the controller 30 such as the transmitter 14, the receiver 16, the element data storage 20, the element data processing section 22, the sound velocity corrector 24, the image generator 26 and the display controller 27, and stores operation programs and processing programs for causing the processing and operations of each part to be executed. A recording medium such as a hard disk, a flexible disk, an MO (Magneto-Optical disk), an MT (Magnetic Tape), a RAM (Random Access Memory), a CD-ROM (Compact Disc Read Only Memory) or a DVD-ROM (Digital Versatile Disk Read Only Memory) can be used as the storage unit 34.

It should be noted that the element data processing section 22, the sound velocity corrector 24, and the phasing addition section 38, the detection processor 40, the DSC 42 and the image creating section 44 of the image generator 26, and the display controller 27 are formed of a CPU (Central Processing Unit) and operation programs for causing the CPU to perform the various types of processing, but may instead be formed of digital circuits.

Next, the sound velocity corrector 24 provided with the element data processing section 22 illustrated in FIG. 1 will be described.

Figure 2:
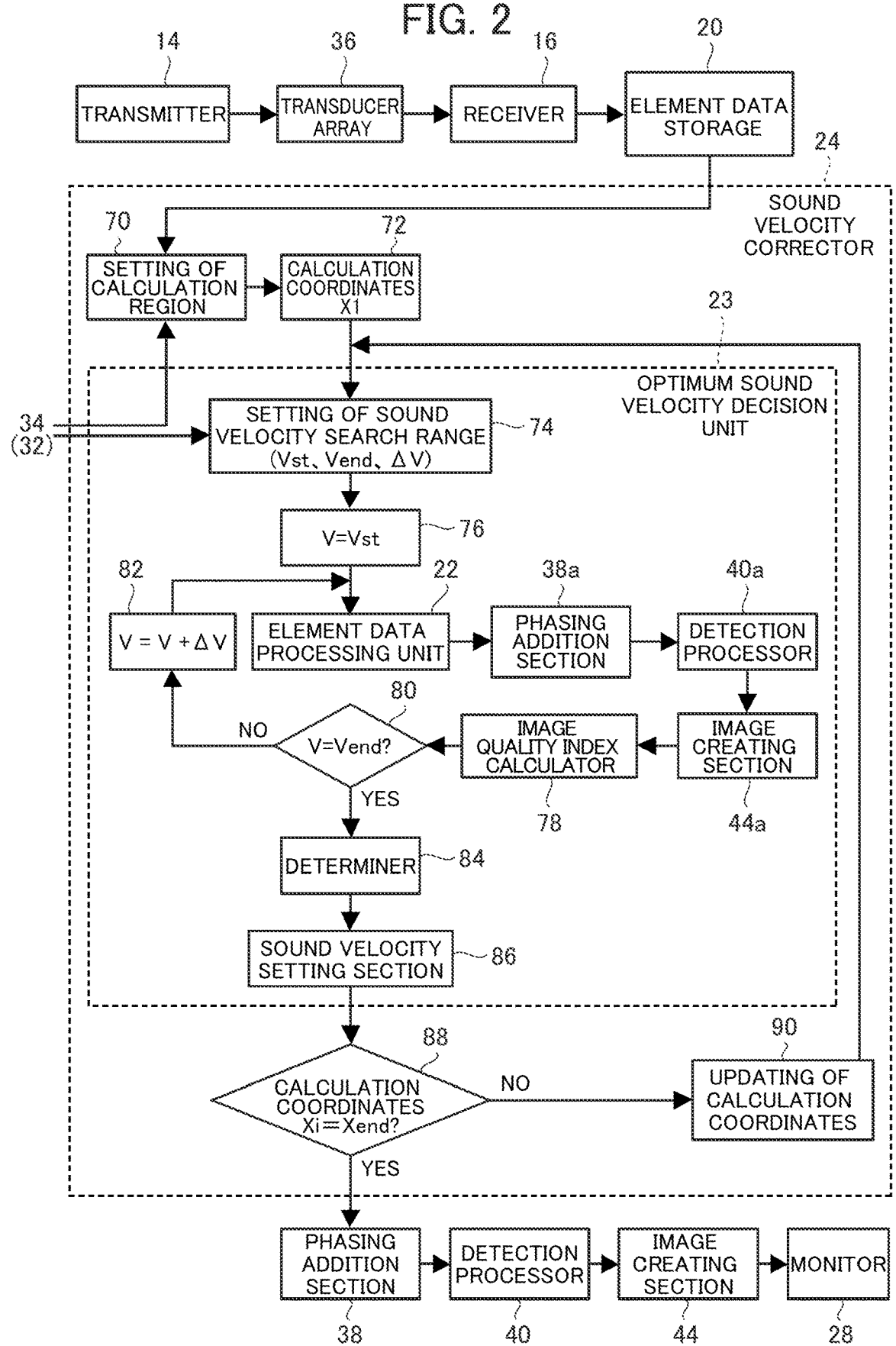
FIG. 2 is a block diagram illustrating, while following a processing flow, principal parts of the ultrasound inspection apparatus of the present invention illustrated in FIG. 1 including a sound velocity corrector, in which an example of the sound velocity corrector is illustrated in detail.

FIG. 2 is a block diagram illustrating, while following a processing flow, principal parts of the ultrasound inspection apparatus including a detailed example of the sound velocity corrector of the ultrasound inspection apparatus of the present invention illustrated in FIG. 1.

The sound velocity corrector 24 comprehensively obtains an optimum sound velocity on the basis of an image quality index (image quality evaluation index) such as the brightness value or sharpness of an image of the inside of the inspection region, and the degree of convergence of sound velocity, by changing an entire predetermined sound velocity range in which a set sound velocity V is estimated as the sound velocity inside the inspection region, at a predetermined change amount of the sound velocity value (sound velocity interval), and, for example, in the case where the target is a living body such as a human body, specifically changing the range from 1400 m/s to 1650 m/s or to 1700 m/s in predetermined increments (steps) of 1 m/s to 50 m/s, for example, in increments of 10 m/s.

For example, the sound velocity correction method disclosed in JP 2011-92686 A can be used as the sound velocity correction method employed by the sound velocity corrector 24. It should be noted that, in the sound velocity correction method disclosed in the aforementioned publication, it is necessary to set a transmission focus for each region of interest. However, in the present invention, since a piece of processed element data is obtained in which transmission focus can be realized in a pseudo manner at any depth through superimposition processing performed by a superimposition processor of the element data processing section 22 inside the sound velocity corrector 24, it is not necessary to set a transmission focus for each calculation region or region of interest. However, in the present invention also, it goes without saying that a transmission focus may be set for each calculation region or region of interest as in the sound velocity correction method disclosed in the aforementioned publication.

In the embodiment illustrated in FIG. 2, the sound velocity corrector 24 includes a calculation area setter 70, an initial calculation coordinate setting section 72, an optimum sound velocity decision unit 23, a final calculation coordinate determiner 88 and a calculation coordinate updater 90, and the optimum sound velocity decision unit 23 includes a sound velocity search range setting section 74, an initial sound velocity value setting section 76, a phasing addition section 38a, a detection processor 40a, an image creating section 44a, an image quality index calculator 78, a final sound velocity value determiner 80, a sound velocity value updater 82, an optimum sound velocity determiner 84 and a sound velocity setting section 86.

In the sound velocity corrector 24, as illustrated in FIG. 2, a set sound velocity V is changed at calculation coordinates X1 to Xend inside the inspection region, sound ray signals are generated for the respective set sound velocities V by performing reception focus processing and phasing addition in the phasing addition section 38a using a piece of processed element data obtained by subjecting a piece of unprocessed element data supplied from the element data storage 20 to multiline processing in the element data processing section 22, on the basis of the set velocities V, ultrasound images are formed in the image creating section 44a from these sound ray signals, and image quality indices such as the brightness value or sharpness of the ultrasound images of the inside of the inspection region at the respective set sound velocities V are calculated.

In the sound velocity corrector 24, the image quality indices such as the brightness value or sharpness of the ultrasound images at the respective set sound velocities V are compared in the optimum sound velocity determiner 84, and, for example, the set sound velocity V for which the obtained value of the image quality index such as the brightness value or sharpness is highest is determined, and this determined set sound velocity V is set as the optimum sound velocity value in the sound velocity setting section 86.

It should be noted that, in the sound velocity corrector 24, changing of the sound velocity value and setting of the optimum sound velocity may be comprehensively performed as illustrated in FIG. 2 or performed in an exploratory manner.

In addition, when changing the sound velocity value and setting the optimum sound velocity in the sound velocity corrector 24, the region and calculation coordinates where the sound velocity value is to be set are not particularly limited and the entire subject or entire inspection region may be set with the same sound velocity value, or the subject or inspection region may be divided into minute regions and a sound velocity value may be set for each minute region, or sound velocity values may be set in units of pixels.

First, the element data processing section 22 of the sound velocity corrector 24 illustrated in FIG. 2 will be described in detail on the basis of FIG. 3.

As illustrated in the figure, the element data processing section 22 is for performing multiline processing and includes a delay time calculator 48 and a superimposition processor 50.

It should be noted that, here, it is assumed that the calculation coordinates inside the inspection region of the subject where multiline processing is to be performed by the element data processing section 22 are set in advance to initial calculation coordinates X1 by the initial calculation coordinate setting section 72 or to calculation coordinates Xi (i=2 to end; hereinafter, represented by calculation coordinates Xi (i=1 to end)) updated by the calculation coordinate updater 90, and it is assumed that the sound velocity value is set in advance to an initial sound velocity value Vst by the initial sound velocity value setting section 76 or to a sound velocity value V (hereinafter, represented by sound velocity value X) updated by the sound velocity value updater 82. In addition, it is assumed that a piece of unprocessed element data relating to the calculation coordinates Xi, which is required for the multiline processing in the element data processing section 22, is read out and then supplied from the element data storage 20.

The delay time calculator 48 acquires, in advance, information relating to the plurality of ultrasound elements of the transducer array 36 of the probe 12, the focal positions of ultrasonic beams, the transmission openings and reception openings of the transducer array 36, and the like input from the operating section 32 or input from the operating section 32 and stored in the storage unit 34, and for the sound velocity at the calculation coordinates Xi inside the inspection region of the subject, uses the sound velocity value V (Vst) set in advance by the initial sound velocity value setting section 76 or the sound velocity value updater 82, to calculate delay times of element data received by the respective ultrasound elements of the reception openings, on the basis of the geometrical arrangement of ultrasound elements of the transmission openings (transmission elements) that form and transmit ultrasonic beams and ultrasound elements of the reception openings that receive ultrasonic echoes produced by the ultrasonic beams from the subject.

The superimposition processor 50 reads out two or more pieces of unprocessed element data generated for the respective two or more target regions, which have been stored and retained by the element data storage 20, on the basis of information relating to multiline processing of element data such as the number of pieces of element data to be superimposed and the superimposition processing method, input from the operating section 32 or input from the operating section 32 and stored in the storage unit 34, and generates a piece of processed element data by superimposing two or more pieces of unprocessed element data in terms of their reception times, namely by matching their reception times, on the basis of the delay times calculated in the delay time calculator 48, and by matching the absolute positions of the elements of the probe at which receiving has been carried out.

Next, multiline processing of element data performed by the element data processing section 22 will be described in detail.

First, a description will be given regarding the relationship between ultrasonic beams (hereinafter, referred to as transmission beams) from transmission ultrasound elements (hereinafter, referred to simply as transmission elements) of the transducer array 36 of the ultrasound probe 12 and a piece of element data obtained by reception ultrasound elements (hereinafter, referred to simply as reception elements) of the transducer array 36 in the case where the piece of element data is obtained by transmitting the transmission beams from the transmission elements to the subject and receiving ultrasonic echoes generated by the interaction between the transmission beams and the subject with the reception elements.

As illustrated in FIGS. 4A and 4C, when acquiring a piece of element data by receiving an ultrasonic echo by using the seven ultrasound elements (hereinafter, also referred to simply as elements) 52a to 52g and the seven ultrasound elements 52b to 52h as reception elements, with regard to an ideal case where a transmission beam 56 transmitted to an inspection region including a reflection point 54 is ideally narrowed down to be less than or equal to an element spacing, as illustrated in FIG. 4A, in the case where a piece of element data is acquired by transmitting the transmission beam 56 with the element 52d in the center of the elements 52a to 52g and directly above the reflection point 54 inside the inspection region serving as a transmission element and receiving an ultrasonic echo with the reception elements 52a to 52g, a focal point 58 of the transmission beam 56 lies on a straight line that connects the element 52d and the reflection point 54 and the transmission beam 56 is transmitted to the reflection point 54, and therefore an ultrasonic echo that is reflected from the reflection point 54 is generated. The ultrasonic echo from the reflection point 54 is received by the reception elements 52a to 52g via a reception path 60 that spread out by a predetermined angle, and a piece of element data 62 such as that illustrated in FIG. 4B is obtained by the reception elements 52a to 52g.

In contrast, as illustrated in FIG. 4C, in the case where the center of the transmission element is shifted in the direction of the elements (rightward direction in the figure) by one element with respect to the reflection point 54, the transmission beam 56 is transmitted with the element 52e, which is adjacent to the element 52d that is directly above the reflection point 54, serving as the transmission element, and an ultrasonic echo is received by the reception elements 52b to 52h, since the reflection point 54 does not exist in a transmission direction of the transmission beam 56, that is, on a straight line that connects the transmission element 52e and the focal point 58, the transmission beam 56 is not transmitted to the reflection point 54. Consequently, an ultrasonic echo reflected from the reflection point 54 is not generated and an ultrasonic echo is not received by the reception elements 52b to 52h, and therefore, as illustrated in FIG. 4D, a piece of element data is not obtained.

However, as illustrated in FIGS. 5A and 5C, an actual transmission beam 64 has a width that is larger than the element spacing.

Here, as in FIG. 5A, in the case where a transmission beam 64 is transmitted with the element 52d, which is directly above the reflection point 54, serving as a transmission element, as in the case illustrated in FIG. 4A, even though the transmission beam 64 has a large width, the focal point 58 thereof lies on a straight line that connects the element 52d and the reflection point 54, and the transmission beam 64 is reflected by the reflection point 54 and an ultrasonic echo is generated. As a result, as in the case illustrated in FIG. 4A, the ultrasonic echo from the reflection point 54 is received by the reception elements 52a to 52g via the reception path 60 that spreads out by a predetermined angle, and a piece of true element data 66 such as that illustrated in FIG. 5B is obtained by the reception elements 52a to 52g.

On the other hand, as illustrated in FIG. 5C, as in the case illustrated in FIG. 4C, in the case where the center of the transmission element is shifted in the direction of the elements (rightward direction in the figure) by one element with respect to the reflection point 54, the transmission beam 64 is transmitted with the element 52e, which is adjacent to the element 52d that is directly above the reflection point 54, serving as the transmission element, and an ultrasonic echo is received by the reception elements 52b to 52h, since the transmission beam 64 has a large width, the transmission beam 64 is transmitted to the reflection point 54 even though the reflection point 54 does not lie in the transmission direction of the transmission beam 64, that is, does not lie on a straight line connecting the transmission element 52e and the focal point 58. Consequently, an ultrasonic echo, which does not originally exist, from the reflection point 54, a so-called ghost reflection signal, is generated and the ghost reflection signal from the reflection point 54 is received by the reception elements 52b to 52h via the reception path 60, which spreads out by a predetermined angle, and a piece of ghost element data 68 such as that illustrated in FIG. 5D is obtained by the reception elements 52b to 52h.

Such a piece of ghost element data 68 causes the precision of an ultrasound image generated from the element data to be decreased.

Here, the sum (propagation distance) of the transmission path along which the transmission beam 64 reaches the reflection point 54 from the transmission element 52e via the focal point 58 and the reception path along which a ghost reflection signal reaches the reception elements 52b to 52h from the reflection point 54 as illustrated in FIG. 5C is longer than the sum (propagation distance) of the transmission path along which the transmission beam 64 reaches the reflection point 54 from the transmission element 52d via the focal point 58 and the reception path along which a true reflection ultrasonic echo from the reflection point 54 reaches the reception elements 52a to 52g as illustrated in FIG. 5A, and therefore the piece of ghost element data 68 such as that illustrated in FIG. 5D is delayed with respect to the piece of true element data 66 such as that illustrated in FIG. 5B.

In the delay time calculator 48 of the element data processing section 22 of the present invention, the time difference between the piece of true element data and the piece of ghost element data, namely the delay time, is calculated from the geometrical arrangement of the transmission element, the focal point of the ultrasonic beam, the reflection point of the subject and the reception elements. Therefore, information on the shape (element spacing, linear, convex, and so forth), focal position, transmission openings, reception openings, and so forth of the ultrasound probe 12 and the sound velocity value of the inspection region of the subject are needed to calculate the delay time, and the delay time calculator 48 acquires these pieces of information, which are input by the operating section 32 or stored in the storage unit 34, and a sound velocity value V set in advance by the sound velocity value updater 82 and the like, and then calculates the delay time. The delay time can be calculated using the sound velocity value V, from a difference in propagation time calculated using the sound velocity and the sum of the lengths (propagation distance) of a transmission path of a transmission beam from the transmission element to the reflection point via the focal point and a reflection path of a true reflection ultrasonic echo or a ghost reflection signal from the reflection point to the reception element, which are calculated from the geometrical arrangement of, for example, the transmission element, the focal point of the ultrasonic beam, the reflection point of the subject and the reception elements.

Figure 6A:
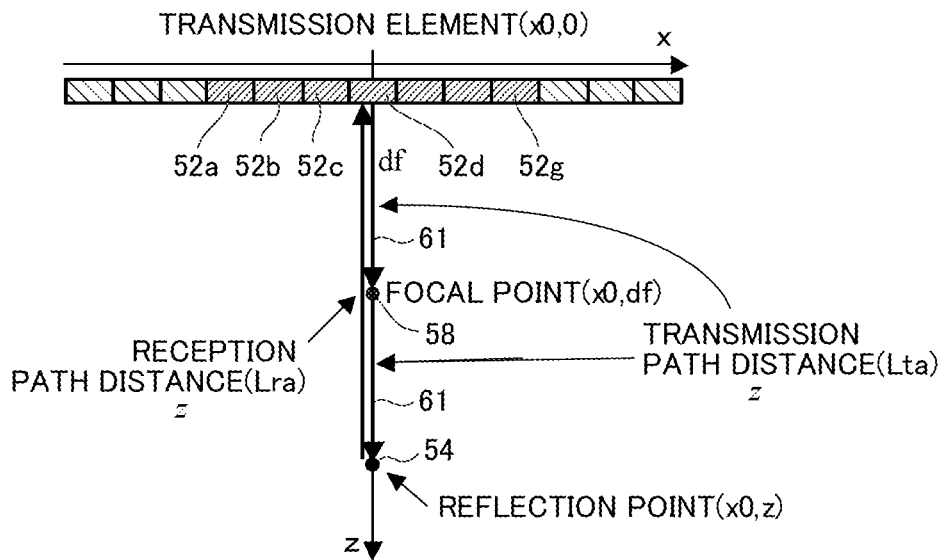
FIGS. 6A and 6B are explanatory diagrams for explaining transmission path and reception path distances of an ultrasonic beam in the cases of a true reflected ultrasonic echo and a ghost reflected signal, respectively.
Figure 6B:
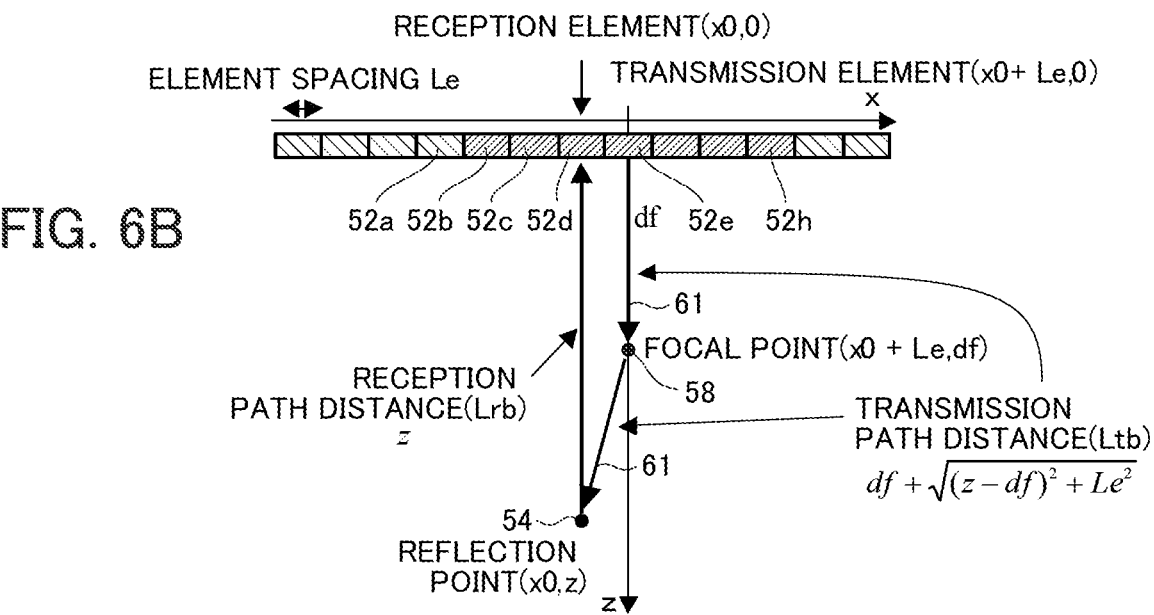

In the present invention, for example, the lengths of the transmission path and reception path of a transmission beam in the cases of a true reflection ultrasonic echo and a ghost reflection signal can be obtained as illustrated in FIGS. 6A and 6B.

In the case of a true reflection ultrasonic echo, as illustrated in FIG. 6A, when a transmission element 52d and a reception element 52d (in the center of reception elements 52a to 52g) coincide with each other, the focal point 58 and the reflection point 54 are arranged directly below that element 52d, the position of the element 52d directly above the reflection point 54 has coordinates (x0, 0) in two-dimensional xy coordinates, the element spacing is denoted Le, the position of the focal point 58 has coordinates (x0, df), the position of the reflection point 54 has coordinates (x0, z), the position of the transmission element 52d also has the coordinates (x0, 0) that are the same as the element 52d directly above the reflection point 54, and a length (transmission path distance) Lta of a transmission path 61 of a transmission beam from the transmission element 52d to the reflection point 54 via the focal point 58 and a length (reception path distance) Lra of a reception path 60 of a true reflection ultrasonic echo from the reflection point 54 to the reception element 52d can be calculated from Lta=Lra=z.

Therefore, the propagation distance Lua of an ultrasonic wave in the case of a true reflection ultrasonic echo is Lua=Lta+Lra=2z.

In the case of a ghost reflection signal, as illustrated in FIG. 6B, compared with the case in FIG. 6A, the position of the transmission element 52e is shifted one element horizontally (x direction: rightward direction in the figure) with respect to the reflection point 54, and the focal point 58 is arranged directly below the transmission element 52e; however, the reflection point 54 is arranged directly below the reception element 52*d*, and when the position of the reception element 52*d* directly above the reflection point 54 has coordinates (x0, 0) in two-dimensional xy coordinates the same as in the case in FIG. 6A, the element spacing is denoted by Le and the position of the reflection point 54 has coordinates (x0, z), the position of the transmission element 52*e* has coordinates (x0+Le, 0), and the position of the focal point 58 has coordinates (x0+Le, df), and therefore a length (transmission path distance) Ltb of the transmission path 61 of a transmission beam from the transmission element 52*e* to the reflection point 54 via the focal point 58 can be calculated from Ltb=df+√{(z−df)$^2$+Le$^2$} and a length (reception path distance) Lrb of a reception path 60 of a ghost reflection signal from the reflection point 54 to the reception element 52*d* can be calculated from Lrb=z.

Therefore, a propagation distance Lub of an ultrasonic wave in the case of a ghost reflection signal is Lub=Ltb+Lrb=df+√{(z−df)$^2$+Le$^2$}+z.

Thus, the propagation time of the true reflection ultrasonic echo is obtained by dividing the propagation distance Lua of an ultrasonic wave, which is obtained by summing together the distance Lta of the transmission path 61 and the distance Lra of the reception path 60 obtained using the geometrical arrangement illustrated in FIG. 6A, by the sound velocity, and the propagation time of the ghost reflection signal is obtained by dividing the propagation distance Lub of an ultrasonic wave, which is obtained by summing together the distance Ltb of the transmission path 61 and the distance Lrb of the reception path 60 obtained using the geometrical arrangement illustrated in FIG. 6B, by the sound velocity. As for the calculation of the delay time, the delay time is obtained from the difference between the propagation time of a true ultrasonic echo when the x coordinates of the reflection point 54 and the transmission element 52 (52*d*) coincide with each other and the propagation time of the ghost reflection signal when the x coordinates of the reflection point 54 and the transmission element 52 (52*e*) are shifted from each other by one element spacing.

It should be noted that, in the geometrical models illustrated in FIGS. 6A and 6B, the transmission path 61 is modeled as going via the focal point 58; however, the present invention is not limited thereto and, for example, there may be a path that directly reaches the reflection point 54 without going via the focal point 58.

In addition, the geometrical models illustrated in FIGS. 6A and 6B are for the case of a linear probe; however, without being limited thereto, a similar geometrical calculation can also be performed for another type of probe from the shape of the probe. For example, in the case of a convex probe, the calculation can be performed in a similar way by setting up a geometrical model from the radius of the probe and the angle of the element spacing.

Furthermore, in the case of steer transmission, a geometrical model (not illustrated) taking into consideration information such as a transmission angle is used, so that delay times of element data of a true ultrasonic echo and of element data of a ghost around the true ultrasonic echo can be calculated from the positional relationship between the transmission element and the reflection point.

In addition, without being limited to a method of calculating the delay time using a geometrical model, delay times under all measurement conditions may be obtained in advance from measurement results of measuring high-brightness reflection points in accordance with the measurement conditions of the apparatus, these delay times may then be stored inside the apparatus, and therefore the delay time obtained under the same measurement condition may then be read out.

Figure 6C:
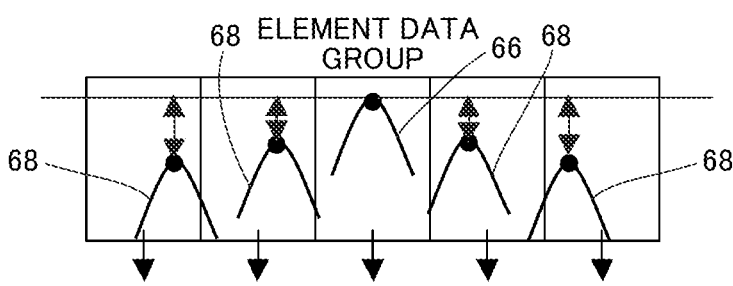
FIGS. 6C and 6D are explanatory diagrams illustrating pieces of element data obtained by a plurality of elements and delay times thereof, respectively.
Figure 6D:
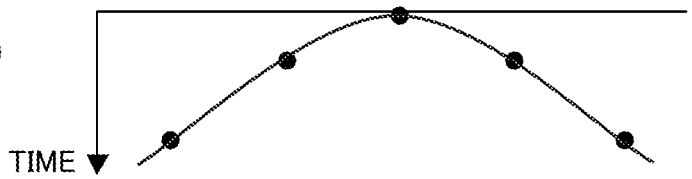
Figure 8:
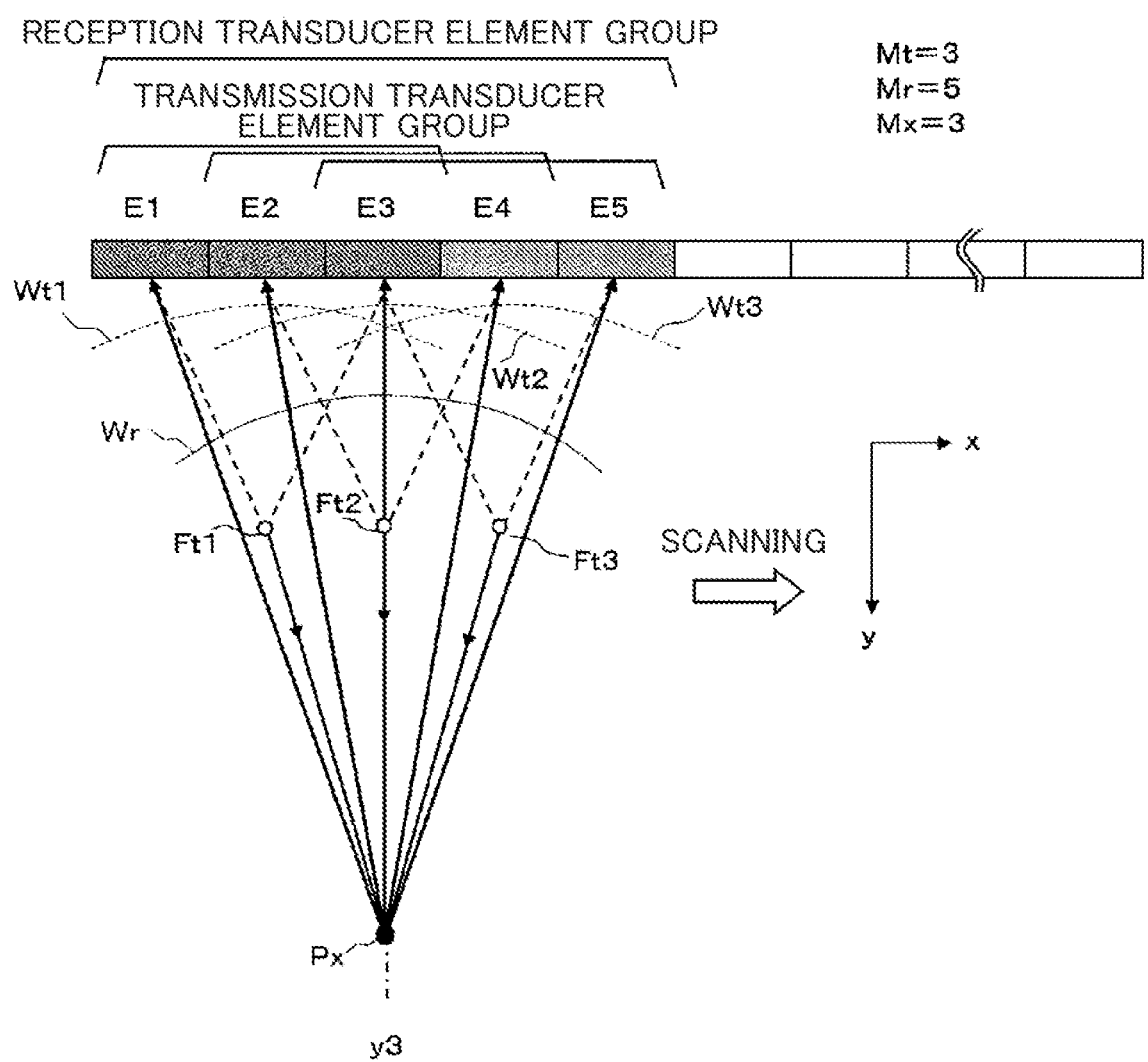
FIG. 8 is an explanatory diagram for explaining transmission and reception of ultrasound waves in an ultrasound diagnostic apparatus of the related art.

The piece of element data 66 of the true signal is illustrated in the center and the piece of element data 68 of the ghost around the true signal is illustrated in FIG. 6C, and an example of the delay time of the element data 68 of the ghost with respect to the element data 66 obtained from the aforementioned geometrical calculation is illustrated in FIG. 6D. It is illustrated that the piece of element data 68 of the ghost signal is symmetrically delayed around the piece of element data 66 of the true signal.

It should be noted that the delay time calculated in the delay time calculator 48 of the element data processing section 22 in this way can also be used in delay correction in the phasing addition section 38.

Next, superimposition processing is performed in the superimposition processor 50 of the element data processing section 22 of the present invention on the piece of element data of the true ultrasonic echo and the piece of element data of the surrounding ghost by using the delay time calculated in the delay time calculator 48 in this way.

In the superimposition processing performed in the superimposition processor 50, information on the number of pieces of superimposition element data and the superimposition processing method at the time when superimposition is to be performed is needed, and these may be input by the operating section 32 or stored in the storage unit 34 in advance.

It should be noted that, although it is preferable for the range of superimposition element data used when superimposition is performed in the superimposition processor 50 to be a piece of element data of a range within a region targeted for sound velocity correction calculation and set by the calculation area setter 70, the range is not limited by the region set by the calculation area setter 70. For example, superimposition may be performed in a range such that pieces of element data to be superimposed overlap each other in adjacent regions.

In FIGS. 7A to 7H, a specific example of superimposition processing performed by the superimposition processor 50 is illustrated for the case where there are five pieces of element data and there are three pieces of superimposition element data.

FIG. 7A illustrates five pieces of element data in a line in the horizontal direction, and illustrates that an ultrasonic beam is transmitted and a reflection signal is received for each piece of element data. The horizontal axis of each piece of element data represents reception elements, and the element in the center at the time of transmission of the ultrasonic beam is illustrated in the center for each piece of element data. The vertical axis represents reception time.

In the central piece of element data among the five pieces of element data, there is a reflection point directly under the element in the center of the element data (element in the center of the reception elements), that is, the element in the center at the time of transmission (transmission element), and a reflection signal is reflected from this reflection point. In short, this reflection signal is a true signal and the piece of central element data represents the true signal.

Regarding the two pieces of element data on either side of the central piece of element data, there is no reflection point directly under the central element at the time of transmission; however, a reflection signal, namely a ghost, generated by the ultrasound beam hitting the reflection point directly under the transmission element of the element data in the center is projected due to the spread of the transmitted ultrasonic beam. The propagation time of the ultrasonic wave of the ghost up to the reflection point becomes longer the further the ghost is from the true signal, and therefore the reception time is delayed compared with the true signal. In addition, although the position of a reception element that first receives a reflection signal from the reflection point is at an element directly above the reflection point, because the horizontal axis of the element data is centered on the central element at the time of transmission of the ultrasonic beam, this central element is shifted by one element for transmission for each piece of element data, and therefore the absolute position of the element is shifted by one element in each piece of element data. That is, although the reception element at which the reflection signal from the reflection point is first received is the central element for the central piece of element data, the reception element is shifted by one element from the central piece of element data for two adjacent pieces of element data, with the reception element being shifted to the left by one element in the right-side element data and being shifted to the right by one element in the left-side element data. In addition, for the pieces of element data on the both ends, the reception element is shifted by two elements from the central piece of element data, with the reception element being shifted to the left by two elements for the piece of element data on the right end and being shifted to the right by two elements for the piece of element data on the left end. In this way, not only is the reception time of the ghost signal delayed with respect to the true signal, there is also a shift with respect to the reception element direction.

FIG. 7B illustrates an example of the delay time of reception time with respect to the central piece of element data among the five pieces of element data illustrated in FIG. 7A.

In the superimposition processor 50, in the case where the piece of element data of an element of interest is the piece of central element data, delay time correction is performed centering on the piece of element data of the element of interest for the number of pieces of superimposition element data, namely for three pieces of element data in the illustrated example, using the delay times illustrated in FIG. 7B, and in addition the pieces of unprocessed element data for the three pieces of element data are superimposed by shifting each piece of element data in the horizontal direction by one element on both sides in the illustrated example, in accordance with the difference in element position with the element of interest (difference in position from central element), namely by matching their phases, and one piece of superimposition processed element data is obtained for the piece of element data of the element of interest.

The piece of thus-obtained superimposition processed element data for the piece of element data of the element of interest is illustrated in FIG. 7C.

Since the piece of element data of the element of interest illustrated in FIG. 7A is a piece of element data of a true signal, when phase matching is performed by carrying out delay time correction and a horizontal shift for the pieces of unprocessed element data of the adjacent element data on both sides of the piece of element data of the element of interest, as illustrated in FIG. 7C, the pieces of unprocessed element data of adjacent element data and the piece of unprocessed element data of the element of interest are superimposed at a position of high brightness because their phases match. Therefore, when these pieces of element data are added together for example, the element data value exhibits a large value (high brightness value) and, for example, even if they are averaged to obtain the average value, an enhanced value (high brightness value) is exhibited.

In contrast, the pieces of element data in FIG. 7D is the same as those in FIG. 7A, and an example of a case is illustrated in which the piece of element data on the left of the piece of central element data, in other words a ghost, is taken as the piece of element data of the element of interest.

FIG. 7E that is the same as FIG. 7B illustrates an example of delay times of reception times with respect to the piece of central element data among the five pieces of element data illustrated in FIG. 7A. That is, FIG. 7A and FIG. 7D illustrate the same pieces of element data, and therefore the delay times of the reception times with respect to the piece of central element data among the five pieces of element data illustrated in FIG. 7D are also the same.

In the superimposition processor 50, using the delay times illustrated in FIG. 7E (that is, the same as FIG. 7B), delay time correction is performed on pieces of element data to be superimposed, centering on the piece of element data of the element of interest, namely three pieces of element data in the illustrated example, and in addition, in accordance with the difference in element position with the element of interest (difference in position from central piece of element), pieces of element data are shifted to both sides in the horizontal direction by one element in the illustrated example so that pieces of unprocessed element data corresponding to the three pieces of element data are superimposed to obtain one piece of superimposition processed element data of the element of interest.

The thus-obtained piece of superimposition processed element data for the piece of element data of the element of interest is illustrated in FIG. 7F.

Since the piece of element data of the element of interest illustrated in FIG. 7D is a piece of ghost element data, even when phase matching is performed by carrying out delay time correction and a horizontal shift on pieces of unprocessed element data corresponding to the pieces of element data on both sides of and adjacent to the piece of element data of the element of interest, as illustrated in FIG. 7F, the pieces of unprocessed element data corresponding to the pieces of adjacent element data and the piece of unprocessed element data of the element of interest are not superimposed because their phases do not match. Consequently, even when these three pieces of element data are added together for example, their phases do not match, so signals having opposite phases and the like cancel each other out, and the added value is not large and, for example, a small value is exhibited when they are averaged to obtain an average value.

FIG. 7G illustrates a superimposed state of three pieces of element data adjacent to each other for each of the five pieces of element data in the illustrated example, which is the result of performing the same delay time correction and horizontal shift on the other pieces of element data taken as the piece of element data of the element of interest, and FIG. 7H illustrates the result of performing, for example, addition processing or averaging processing as superimposition processing on those pieces of element data.

As illustrated in FIG. 7H, for the piece of element data of the element of interest when the coordinates of the transmission element and the reflection point coincide with each other as illustrated in FIG. 7A, the piece of element data of the true signal is obtained as superimposition processed element data having a high brightness value. For the two pieces of element data on both sides or a total of four pieces of element data, since pieces of ghost element data having a different phase from each other are added together or averaged, they cancel each other out, and therefore the value of piece of ghost superimposition processed element data becomes small with respect to the piece of superimposition processed element data having a high brightness value, which corresponds to the piece of element data of a true signal, and the value can be reduced to the extent that the effect of the piece of the ghost element data on the piece of element data of the true signal can be reduced or to the extent that the effect can be ignored.

Consequently, since it is possible to generate an ultrasound image from pieces of element data with the effect of ghosts eliminated, namely pieces of element data equal to those in which all points on sound rays have a focal point formed thereon, by subjecting pieces of processed element data to phasing addition and detection processing and generating a piece of reception data to generate an ultrasound image, it is possible to generate an ultrasound image with high image quality, high brightness, and excellent sharpness.

It should be noted that, in the present invention, generation of such a piece of processed element data is referred to as multiline processing.

In the present invention, the center element is the element in the center in the azimuth direction in the case where the number of transmission openings (the number of elements which perform the transmission of the ultrasonic waves) is an odd number.

On the other hand, in the case where the number of openings is an even number, any of the elements in the center in the azimuth direction may be taken as the central element, or it may be assumed that there is an element in the center in the azimuth direction and this may be taken as the central element. That is, in the case where the number of openings is an even number, a calculation may be performed with the assumption that there is a focal point on a line in the center of the openings.

It should be noted that, as a superimposition processing method used in the superimposition processor 50, not only values are simply added together, but an average value or a median value may be taken, or values may be added together after being multiplied (weighted) with a coefficient. It should be noted that taking an average value or a median value is considered to correspond to applying an averaging filter or a median filter at the element data level, but an inverse filter or the like carried out in normal image processing may be used instead of the averaging filter or the median filter. Alternatively, pieces of element data to be superimposed may be compared with each other and the largest value may be taken when they are similar, an average value may be taken when they are not similar, and a median value may be taken when there is a biased distribution, and the like, but without being limited to the aforementioned, the superimposition processing may be changed on the basis of the feature quantity of each of the element data to be superimposed.

In addition, the number of pieces of element data to be superimposed with the piece of element data of the element of interest is not limited to two as in the illustrated example and may be one or may be three or more. That is, the number of pieces of element data to be superimposed with the piece of element data of the element of interest may be suitably set in accordance with the required processing speed (frame rate or the like), image quality, or the like.

In addition, it is preferable that the number of pieces of element data to be superimposed be in line with the degree to which the beam width of the ultrasonic beam broadens. Therefore, when the beam width is changed in accordance with the depth, the number of pieces of element data to be superimposed may also be changed in accordance with the depth. In addition, since the beam width depends on the number of transmission openings, the number of pieces of element data to be superimposed may be changed in accordance with the number of transmission openings. Alternatively, the number of pieces of element data to be superimposed may be changed on the basis of the feature quantity such as the brightness value of an image, or the optimum number of pieces of element data to be superimposed may be selected from among images created by changing the number of pieces of element data to be superimposed to a plurality of patterns.

As described above, the phases of signals match for the piece of element data of a true signal as a result of the superimposition, whereas, since the phases of signals do not match for a ghost, the signals of various phases cancel each other out and the signals are weakened as a result of the superimposition processing such as addition. As a result, a true signal has an effective value and, for example, remains as a piece of element data of high brightness, whereas a ghost signal has a weakened value and, for example, can be obtained as a piece of element data of low brightness.

The element data processing section used in the present invention is configured principally as described above.

Returning back to FIG. 2, the description will continue of each part of the sound velocity corrector 24, which comprehensively performs changing of a sound velocity value and setting of an optimum sound velocity.

In the sound velocity corrector 24 illustrated in FIG. 2, the calculation area setter 70 sets a region, for example a region of interest ROI, which is in the inspection region and is to be subjected to a sound velocity correction calculation in accordance with an input through the operating section 32 (refer to FIG. 1) by an operator, or the like, extracts all points that are to be calculation targets on xy coordinates of the set region, and sets the extracted points as calculation coordinates X1 to Xend. Here, as long as each of the regions represented by the calculation coordinates X1 to Xend is a region which is considered to have the same ambient sound velocity, each region is not particularly limited and may be the entire subject or the entire inspection region, or may be a minute region obtained by dividing the subject or the inspection region or may be a single point in units of pixels.

The initial calculation coordinate setting section 72 sets the calculation coordinates Xi to initial calculation coordinates X1 from among the calculation coordinates X1 to Xend set by the calculation area setter 70. The piece of data of the calculation coordinates X1 set by the initial calculation coordinate setting section 72 is sent to the optimum sound velocity decision unit 23.

It should be noted that the calculation area setter 70 is not limited to a configuration in which a calculation region is set in accordance with an input from the operating section 32 and may have a configuration in which, for example, a region of interest ROI is set and made to be a calculation region by analyzing an ultrasound image (B-mode image signal) generated by the image creating section 44 of the image generator 26 (refer to FIG. 1).

For example, the calculation area setter 70 determines that a position (pixel) for which the difference of brightness values of adjacent pixels is equal to or greater than a predetermined value is an edge portion (edge) of a structural region (tissue or lesion) in an ultrasound image generated by the image creating section 44, and determines that a region surrounded by the edges or a region including many edges is a structural region and extracts the region, namely a target portion P, such that the calculation area setter 70 may set a region that includes the target portion and has a predetermined shape and size to be, for example, a region of interest ROI as well as to be a calculation region.

It should be noted that, when the calculation region is set by analyzing an ultrasound image, the structural region may be regarded as being constituted by one type of region, or may be regarded as being constituted by two or more types of regions in accordance with the degree of continuity of edges, the level of brightness value, or the like, and each region may be determined to be the target portion and extracted, and then a region of interest ROI may be set for each target portion and may be set as the calculation region.

The optimum sound velocity decision unit 23 calculates and sets an optimum ambient sound velocity (hereinafter, referred to as an optimum sound velocity value) at the initial calculation coordinates X1 set by the initial calculation coordinate setting section 72 or at the calculation coordinates Xi updated by the calculation coordinate updater 90.

Here, the optimum sound velocity value is a set sound velocity V at which the contrast and/or sharpness of an image is highest when the set sound velocity (set ambient sound velocity) V is subjected to various changes and ultrasound images are formed by reception focus processing being performed on the basis of the respective set sound velocities V; for example, an optimum sound velocity value can be determined on the basis of the contrast of an image, the spatial frequency in the scanning direction, scattering, and the like, as described in JP 8-317926 A.

The optimum sound velocity decision unit 23 is for comprehensively obtaining and setting an optimum ambient sound velocity value (hereinafter, also referred to as an optimum sound velocity value) as an output value, by using a piece of unprocessed element data relating to the calculation coordinates Xi read out from the element data storage 20, as an input value.

As described above, the optimum sound velocity decision unit 23 may be a unit that sets an optimum sound velocity value by comprehensively searching a predetermined sound velocity search range, and includes the sound velocity search range setting section 74, the initial sound velocity value setting section 76, the element data processing section 22, the phasing addition section 38a, the detection processor 40a, the image creating section 44a, the image quality index calculator 78, the final sound velocity value determiner 80, the optimum sound velocity determiner 84, the sound velocity value updater 82, and the sound velocity setting section 86.

The sound velocity search range setting section 74 is for setting a search range (initial sound velocity value and final sound velocity value) of an ambient sound velocity at the calculation coordinates Xi and for setting a change amount for the sound velocity value (sound velocity interval). The sound velocity search range setting section 74, for example, sets an initial sound velocity value Vst at which to start the sound velocity search, a final sound velocity value Vend at which to end the sound velocity search, and a step amount (sound velocity change amount: sound velocity interval) $\Delta V$ by which the set sound velocity V is to be changed. As an example, in the case of a living body, the sound velocity search range setting section 74 can set the initial sound velocity value Vst to 1400 m/s, the final sound velocity value Vend to 1700 m/s, and the sound velocity change amount $\Delta V$ to 10 m/s, for example.

It should be noted that the initial sound velocity value Vst, the final sound velocity value Vend, and the sound velocity change amount $\Delta V$ set by the sound velocity search range setting section 74 are not limited to the aforementioned values and may be determined in accordance with the subject, the inspection region of the subject, the calculation coordinates Xi of the region, and the like. In addition, the initial sound velocity value Vst, the final sound velocity value Vend, and the sound velocity change amount $\Delta V$ may be input by an operator via the operating section 32 to the sound velocity search range setting section 74 in accordance with the subject, the inspection region of the subject, calculation coordinates Xi of the region, and the like, or may be read out in advance from among information stored in the storage unit 34.

The initial sound velocity value setting section 76 sets the set sound velocity V to the initial sound velocity value Vst set by the sound velocity search range setting section 74. In the case of a living body described above, the initial sound velocity value setting section 76 sets the set sound velocity V to 1400 m/s as the initial sound velocity value Vst. A piece of data of the initial sound velocity value Vst set by the initial sound velocity value setting section 76 is sent to the downstream element data processing section 22.

The phasing addition section 38a has completely the same configuration and function as the phasing addition section 38, and generates sound ray signals by performing reception focus processing in which a delay is added, on the basis of the optimum sound velocity set by the sound velocity corrector 24, to pieces of processed element data relating to the calculation coordinates Xi obtained by the element data processing section 22 using the set sound velocity V and the pieces of processed element data are added together.

The detection processor 40a has completely the same configuration and function as the detection processor 40a, and generates a piece of B-mode image data, which is tomographic image information relating to tissues inside the subject, by performing processing such as envelope detection processing on the sound ray signals generated by the phasing addition section 38a.

The image creating section 44a has completely the same configuration and function as the image creating section 44, and creates an ultrasound image by performing image processing on the piece of B-mode image data generated by the detection processor 40a.

The image quality index calculator 78 calculates an image quality index at the set sound velocity V from the ultrasound image created by the image creating section 44a, that is, calculates an image quality index such as a brightness value or sharpness of an image, more specifically, for example, the sharpness of an image at the calculation coordinates Xi (for example, region of interest ROI) at each set sound velocity V. The calculated image quality index is stored inside the image quality index calculator 78 in association with the set sound velocity V and, for example, is stored in a memory inside the image quality index calculator 78.

The final sound velocity value determiner 80 compares the set sound velocity V with the final sound velocity value Vend and determines whether the two values are equal to each other. In the case where the set sound velocity V is not equal to the final sound velocity value Vend (V≠Vend), it proceeds to the sound velocity value updater 82, and in the case where the set sound velocity V is equal to the final sound velocity value Vend (V=Vend), it proceeds to the optimum sound velocity determiner 84.

The sound velocity value updater 82 sets a new set sound velocity V (V=V+$\Delta V$) by adding the sound velocity change amount $\Delta V$ to the current set sound velocity V. A piece of data of the set sound velocity V (V=V+$\Delta V$) updated and set by the sound velocity value updater 82 is sent to the upstream element data processing section 22.

The optimum sound velocity determiner 84 reads out the image quality indices obtained for the respective sound velocity values V (Vst to Vend) stored in the image quality index calculator 78, compares the image quality indices at the respective set sound velocities V, for example, compares the sharpness (sharpness values) of the ultrasound image, and determines a set sound velocity V when the image quality is best, for example, when the sharpness (sharpness value) of the ultrasound image is highest.

The sound velocity setting section 86 sets, as the optimum sound velocity value, the set sound velocity V at which it has been determined in the optimum sound velocity determiner 84 that the image quality of a generated ultrasound image is best.

It should be noted that, in the optimum sound velocity decision unit 23 illustrated in FIG. 2, processing is performed with the set sound velocity V being repeatedly changed; however, the present invention is not limited thereto, and all of the sound velocity values to be searched may be calculated in parallel using multithreading such as with a GPU (Graphics Processing Unit), and image quality indices may be obtained for all of the sound velocity values at one time.

The optimum sound velocity decision unit 23 sets the optimum sound velocity value corresponding to the calculation coordinates Xi in the sound velocity setting section 86, and then it proceeds to the final calculation coordinate determiner 88.

The optimum sound velocity decision unit 23 is configured principally as described above and calculates an optimum sound velocity value for the calculation coordinates Xi.

The final calculation coordinate determiner 88 compares the calculation coordinates Xi with the final calculation coordinates Xend and determines whether the two sets of calculation coordinates are equal to each other. In the case where the calculation coordinates Xi are not equal to the final calculation coordinates Xend (X≠Xend), it proceeds to the calculation coordinate updater 90, and in the case where the calculation coordinates Xi are equal to the final calculation coordinates Xend (X=Xend), it proceeds to the phasing addition section 38 of the image generator 26, and the optimum sound velocity values calculated for the respective calculation coordinates X1 to Xend and pieces of processed element data processed by the element data processing section 22 using the optimum sound velocity values are supplied to the phasing addition section 38 together with pieces of coordinate data of the respective calculation coordinates X1 to Xend.

The calculation coordinate updater 90 updates the current calculation coordinates Xi to the next new calculation coordinates Xi+1. A piece of data of the next new calculation coordinates Xi+1 updated by the calculation coordinate updater 90 is sent to the sound velocity search range setting section 74 of the upstream optimum sound velocity decision unit 23.

The sound velocity corrector 24 is configured principally as described above and calculates optimum sound velocity values for all of the respective calculation coordinates Xi (i=1 to end) and pieces of processed element data.

It should be noted that, as described above, optimum ambient sound velocities can be obtained by including not only sound velocities from the reflection point (sampling point, observation point) up to the reception elements of the transducer array 36 of the ultrasound probe 12 but also sound velocities from the transmission elements of the transducer array 36, which form virtual point sound sources up to the reflection point, by incorporating the element data processing section 22 that performs multiline processing in the loop of searching for an optimum sound velocity in sound velocity correction performed by the sound velocity corrector 24 of the ultrasound inspection apparatus 10 of the present embodiment, and using sound velocity values searched by the sound velocity corrector 24, as sound velocity values when calculating delay time correction at the time of multiline processing.

The ultrasound inspection apparatus of the present invention is configured principally as described above, and hereinafter the operation and action of the ultrasound inspection apparatus of the present invention and the ultrasound inspection method of the present invention will be described while referring to FIG. 1 and FIG. 2.

When an operator starts measurement by bringing the ultrasound probe 12 illustrated in FIG. 1 into contact with a surface (inspection region) of the subject, an ultrasonic beam is transmitted from a plurality of elements of the transducer array 36 in accordance with driving signals supplied from the transmitter 14. Then, a plurality of elements of the transducer array 36 receives an ultrasonic echo from the subject and outputs an analog element signal as a reception signal.

The receiver 16 amplifies and supplies the analog element signal to the A/D converter 18, the A/D converter 18 converts the analog element signal into a piece of digital element data and supplies the piece of digital element data to the element data storage 20 where the piece of digital element data is stored and retained as a piece of unprocessed element data.

Next, in the sound velocity corrector 24 illustrated in FIG. 2, the calculation coordinates X1 to Xend are set by the calculation area setter 70 in accordance with an input through the operating section 32 (refer to FIG. 1) by the operator, or the like, and then the calculation coordinates Xi are set to the initial calculation coordinates X1 by the initial calculation coordinate setting section 72, and a piece of data of the set calculation coordinates X1 is sent to the optimum sound velocity decision unit 23.

In the optimum sound velocity decision unit 23, first, the sound velocity search range setting section 74 sets the initial sound velocity value Vst, the final sound velocity value Vend, and the sound velocity change amount ΔV, which have been input via the operating section 32 by the operator or have been read out in advance from among information on the sound velocity search range stored in the storage unit 34, in accordance with the subject, the inspection region of the subject, the calculation coordinates of the region Xi, or the like, and, for example, as described above, sets the initial sound velocity value Vst to 1400 m/s, the sound velocity value Vend to 1700 m/s, and the sound velocity change amount ΔV to 10 m/s for a living body.

Next, the initial sound velocity value setting section 76 sets the set sound velocity V to the initial sound velocity value Vst (for example, 1400 m/s), and then it proceeds to the element data processing section 22.

Next, the element data processing section 22 calculates, in the delay time calculator 48 (refer to FIG. 3), delay times of pieces of unprocessed element data of ghost signals around a piece of unprocessed element data of a true signal (for example, FIG. 7B and FIG. 7E, both are the same), from the geometrical arrangement of a transmission element, a focal point, a reflection point and reception elements, and the set sound velocity V set by the initial sound velocity value setting section 76 in advance (for example, calculation using the geometrical model of FIGS. 6A and 6B).

Next, the element data processing section 22 reads out pieces of unprocessed element data relating to the calculation coordinates X1 from the element data storage 20, sets a piece of element data to be processed as a piece of element data of interest, and obtains a piece of processed element data by performing multiline processing by matching the phase of the piece of the element data of interest and the phases of the pieces of surrounding unprocessed element data and superimposing the pieces of phase-matched element data in the superimposition processor 50 (refer to FIG. 3) using the delay times calculated by the delay time calculator 48. Thus, a piece of enhanced processed element data is obtained for a piece of unprocessed element data including a true signal, and a piece of weakened processed element data is obtained for a piece of unprocessed element data of a ghost.

The element data processing section 22 supplies the thus-obtained piece of processed element data to the phasing addition section 38a.

Next, the phasing addition section 38a generates sound ray signals by performing reception focus processing and phasing addition using pieces of processed element data corresponding to the calculation coordinates X1 supplied from the element data processing section 22, on the basis of the set sound velocity V, which is the initial sound velocity value Vst. Next, the detection processor 40a performs detection processing on the generated sound ray signals to generate the B-mode image signal. The image creating section 44a creates an ultrasound image from the generated B-mode image signal.

Thereafter, the image quality index calculator 78 calculates an image quality index such as the brightness value or sharpness of the ultrasound image at the set sound velocity V, from the created ultrasound image, such as calculating the sharpness of the image at Xi (X1) at each set sound velocity V. The calculated image quality index is stored inside the image quality index calculator 78 in association with the set sound velocity V.

Next, the final sound velocity value determiner 80 compares the set sound velocity V with the final sound velocity value Vend and determines whether the two values are equal to each other. In the determination performed by the final sound velocity value determiner 80, in the case where the set sound velocity V is equal to the final sound velocity value Vend (V=Vend), it proceeds to the optimum sound velocity determiner 84, and in the case where the set sound velocity V is not equal to the final sound velocity value Vend (V≠Vend), it proceeds to the sound velocity value updater 82.

In the case where it proceeds to the sound velocity value updater 82, the sound velocity value updater 82 adds the sound velocity change amount ΔV to the current set sound velocity V, and sets the new set sound velocity V (V=V+ΔV).

Thereafter, returning to the element data processing section 22, on the basis of the new set sound velocity, multiline processing by the element data processing section 22, phasing addition by the phasing addition section 38a, detection processing by the detection processor 40a, image creation by the image creating section 44a, calculation and retention of an image quality index by the image quality index calculator 78, and determination by the final sound velocity value determiner 80 are performed.

In the case where the determination result obtained by the final sound velocity value determiner 80 is V≠Vend, as described above, it proceeds to the sound velocity value updater 82 and setting of a new set sound velocity V by the sound velocity value updater 82, multiline processing by the element data processing section 22 on the basis of the new set sound velocity V, phasing addition by the phasing addition section 38a, detection processing by the detection processor 40a, image creation by the image creating section 44a, calculation and retention of an image quality index by the image quality index calculator 78, and determination by the final sound velocity value determiner 80 are repeatedly performed until V=Vend. That is, these processing steps are repeatedly performed while changing the value of the set sound velocity by ΔV each time up to the final sound velocity value Vend indicating the end of the sound velocity range, for example, while changing the set sound velocity V from 1400 m/s to 1700 m/s in increments of 10 m/s.

On the other hand, in the case where the determination result obtained by the final sound velocity value determiner 80 is V=Vend, image quality indices for all of the set sound velocities V within the search range of sound velocity have been obtained, and therefore, as described above, it proceeds to the optimum sound velocity determiner 84, and the optimum sound velocity determiner 84 reads out the image quality indices obtained for the respective sound velocity values retained in the image quality index calculator 78. The optimum sound velocity determiner 84 compares the image quality indices at the respective set sound velocities V, for example, compares the sharpness (sharpness values) of the ultrasound images, and determines a set sound velocity V when the image quality is best, for example, when the sharpness (sharpness value) of the ultrasound image is highest, and the sound velocity setting section 86 employs and sets the set sound velocity V determined by the optimum sound velocity determiner 84 as the optimum sound velocity value.

In this way, the optimum sound velocity decision unit 23 calculates the optimum sound velocity value corresponding to the calculation coordinates Xi (X1).

Next, once calculation of the optimum sound velocity value corresponding to the calculation coordinates Xi (X1) by the optimum sound velocity decision unit 23 is completed, it proceeds to the final calculation coordinate determiner 88.

In the final calculation coordinate determiner 88, the calculation coordinates Xi are compared with the final calculation coordinates Xend and it is determined whether they are equal to each other. As a result of the determination, in the case where the calculation coordinates Xi are not equal to the final calculation coordinates Xend (Xi≠Xend), it proceeds to the calculation coordinate updater 90.

Thereafter, in the calculation coordinate updater 90, the current calculation coordinates Xi are updated to the next new calculation coordinates Xi+1, and it proceeds to the upstream optimum sound velocity decision unit 23.

Thereafter, in the optimum sound velocity decision unit 23, comprehensive searching of set sound velocities V described above is performed, an optimum sound velocity value corresponding to the calculation coordinates Xi+1 is calculated. Then it proceeds to the final calculation coordinate determiner 88 again, and determination for the final calculation coordinates Xend is performed.

In the case where the determination result obtained by the final calculation coordinate determiner 88 is Xi≠Xend, as described above, it proceeds to the calculation coordinate updater 90, and setting of new calculation coordinates Xi by the calculation coordinate updater 90, calculation of an optimum sound velocity value corresponding to the calculation coordinates Xi realized by comprehensively searching set sound velocities V in the optimum sound velocity decision unit 23, and the determination made by the final calculation coordinate determiner 88 are repeatedly performed until Xi=Xend.

On the other hand, as a result of the determination in the final calculation coordinate determiner 88, in the case where the calculation coordinates Xi are equal to the final calculation coordinates Xend (X=Xend), setting of the optimum sound velocity values by the sound velocity corrector 24 is terminated, the optimum sound velocity values and pieces of processed element data corresponding to all of the respective calculation coordinates Xi (i=1 to end) are calculated, and it proceeds to the phasing addition section 38 of the image generator 26. Thus, the optimum sound velocity values calculated for the respective calculation coordinates X1 to Xend and the pieces of processed element data processed by the element data processing section 22 by using the optimum sound velocity values are supplied to the phasing addition section 38 along with respective pieces of coordinates data of the calculation coordinates X1 to Xend.

Next, in the phasing addition section 38 of the image generator 26, a piece of reception data (sound ray signal) is generated by subjecting a piece of the element data to reception focus processing, and the piece of reception data is then supplied to the detection processor 40. In the detection processor 40, a B-mode image signal is generated by processing the sound ray signal. The B-mode image signal is subjected to raster conversion by the DSC 42, the image creating section 44 performs image processing, and an ultrasound image is generated. The generated ultrasound image is stored in the image memory 46, and then the ultrasound image is displayed on the monitor 28 by the display controller 27.

Thus, the ultrasound inspection apparatus of the present invention can obtain a high-quality ultrasound image in which the effect of variations in sound velocity inside living body tissues is reduced and in addition can obtain a sharp ultrasound image having a high resolution independent of the width of the transmission beam, a high SN ratio and an optimum spatial resolution, without using a wide beam transmission-dedicated ultrasound probe and with the frame rate unchanged from that of the related art, since optimum ambient sound velocities are obtained using image quality indices used to evaluate ultrasound images created using pieces of processed element data which has ghost signals weakened and true signals enhanced as a result of being subjected to multiline processing by the element data processing section, and an ultrasound image is created using the pieces of processed element data that has been subjected to multiline processing using the obtained optimum ambient sound velocities.

Next, an ultrasound inspection apparatus of a second working example of the present invention will be described on the basis of FIG. 9 and FIG. 10.

Figure 9:
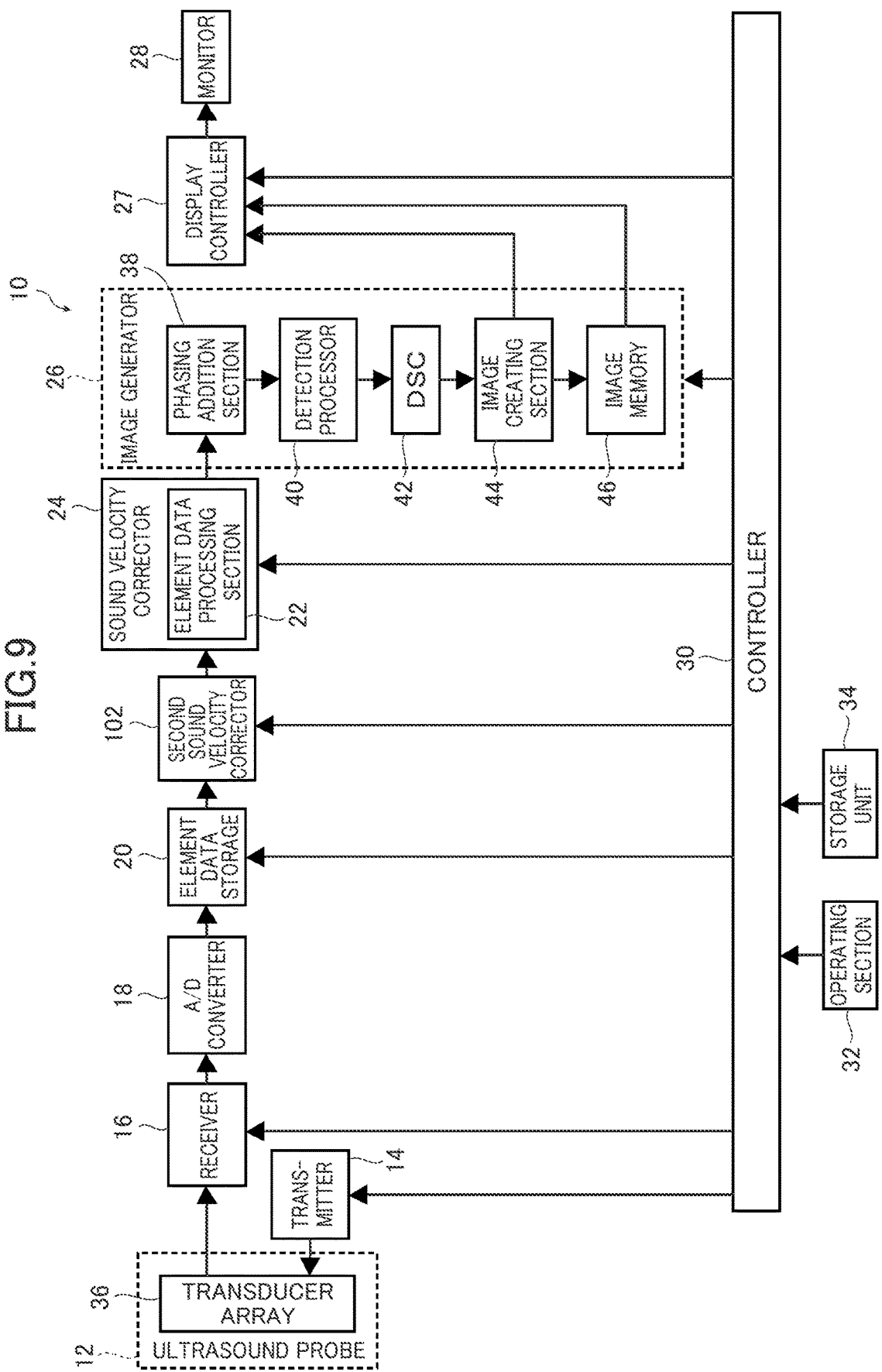
FIG. 9 is a block diagram conceptually illustrating an example of a configuration of a second working example of an ultrasound inspection apparatus according to the present invention.
Figure 10:
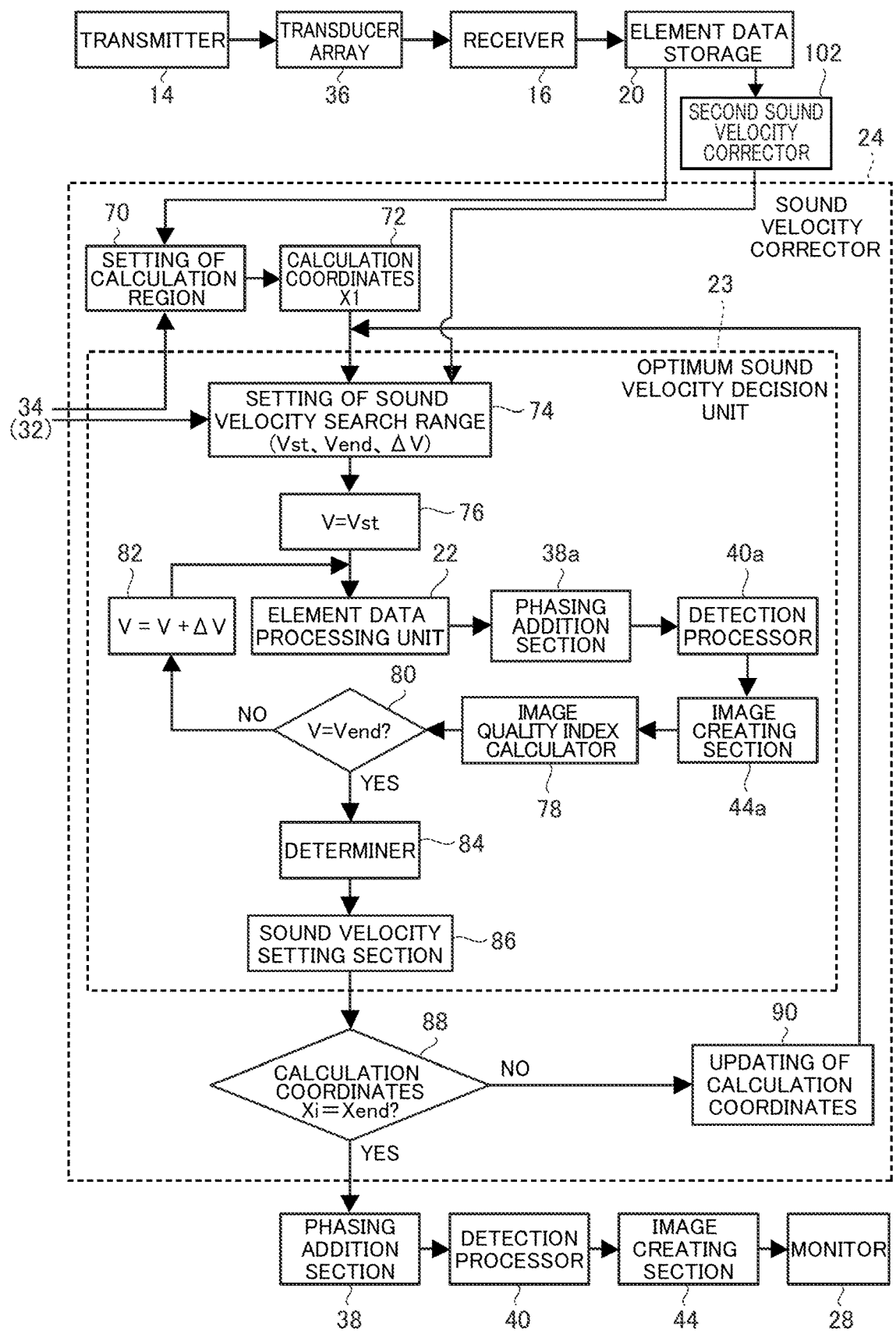
FIG. 10 is a block diagram illustrating, while following a processing flow, principal parts of the ultrasound inspection apparatus of the present invention illustrated in FIG. 9 including a sound velocity corrector, in which an example of the sound velocity corrector is illustrated in detail.

FIG. 9 is a block diagram conceptually illustrating the configuration of the ultrasound inspection apparatus according to the second working example of the present invention, and FIG. 10 is a block diagram conceptually illustrating, while following a processing flow, an example of principle parts of the ultrasound inspection apparatus illustrated in FIG. 9.

It should be noted that an ultrasound inspection apparatus 100 illustrated in FIG. 9 and FIG. 10 has completely the same configuration as the ultrasound inspection apparatus 10 illustrated in FIG. 1 and FIG. 2 except for being provided with a second sound velocity corrector 102, and therefore the same constituent elements are denoted by the same reference numerals and detailed descriptions thereof are omitted.

As illustrated in FIG. 9, the ultrasound inspection apparatus 100 includes an ultrasound probe 12, a transmitter 14 and a receiver 16 connected to the ultrasound probe 12, an A/D converter 18, an element data storage 20, a second sound velocity corrector 102, a sound velocity corrector 24 provided with an element data processing section 22, an image generator 26, a display controller 27, a monitor 28, a controller 30, an operating section 32, and a storage unit 34.

In the ultrasound inspection apparatus 100, a provisional sound velocity value is obtained by performing sound velocity correction using a piece of unprocessed element data (first element data) in the second sound velocity corrector 102 prior to sound velocity correction performed by the sound velocity corrector 24, and an optimum sound velocity value is obtained by using this sound velocity value as an initial value when performing sound velocity correction in the sound velocity corrector 24.

The second sound velocity corrector 102 is connected to the element data storage 20 and to the sound velocity corrector 24 and supplies, to the sound velocity corrector 24, a sound velocity value calculated by performing sound velocity correction using a piece of unprocessed element data (first element data) stored in the element data storage 20.

The sound velocity correction performed by the second sound velocity corrector 102 is not particularly limited and, for example, the method described in JP 2011-92686 A can be used. This method calculates a focus index for each of a plurality of set sound velocities by performing reception focus processing on a piece of unprocessed element data for each set sound velocity, and determines an optimum sound velocity value on the basis of this focus index. That is, the set sound velocity at which a piece of unprocessed element data can be most appropriately subjected to reception focus processing is made to be the optimum sound velocity value.

It should be noted that, since sound velocity correction in the second sound velocity corrector 102 may be roughly obtained as an initial value of a sound velocity search when sound velocity correction is performed in the sound velocity corrector 24, the transmission focus is not necessarily set for each calculation region or each region of interest. In addition, without being limited to being performed for each calculation region or region of interest, a sound velocity value may be obtained with an entire screen taken as a region of interest.

As illustrated in FIG. 10, the second sound velocity corrector 102 supplies the obtained sound velocity value to the sound velocity search range setting section 74 of the optimum sound velocity decision unit 23 of the sound velocity corrector 24.

The sound velocity search range setting section 74 of the optimum sound velocity decision unit 23 sets the sound velocity value supplied from the second sound velocity corrector 102 as the initial sound velocity value Vst.

The sound velocity value updater 82 sequentially sets the initial sound velocity value Vst and sound velocity values (Vst+ΔV) before and after that value, and sets the next set sound velocity on the basis of results for these three sound velocity values obtained by the image quality index calculator 78 calculating image quality indices. For example, if the best result is obtained in the case where the set sound velocity V is Vst+ΔV, the sound velocity value updater 82 sets the next set sound velocity V to Vst+2×ΔV, and if the best result is obtained in the case where the set sound velocity V is Vst, Vst is employed as the optimum sound velocity value. That is, the optimum sound velocity decision unit 23 obtains, in an exploratory manner, an optimum sound velocity value with a sound velocity value supplied from the second sound velocity corrector 102 taken as an initial sound velocity value.

A configuration is employed in which the second sound velocity corrector 102 performs sound velocity correction using a piece of unprocessed element data and a thus-obtained value is used as an initial value of sound velocity correction in the sound velocity corrector 24, whereby the time taken for measuring and calculating an optimum sound velocity value can be reduced.

The present invention has been described hereinabove in detail, and it goes without saying that the present invention is not limited to the aforementioned working examples and various improvements or modifications may be made without departing from the gist of the present invention.

For example, each constituent element illustrated in FIG. 1 and FIG. 2 may be formed as hardware or may be formed as software to be executed by a computer or the like.

In addition, a program for ultrasound inspection that causes a computer to operate in such a way as to function as each constituent element, such as the element data processing section included in the sound velocity corrector described above, and as an image generator, in correspondence to each function of the ultrasound inspection apparatus described in the each embodiment of the present invention, and a program for ultrasound inspection that causes a computer to execute each of the steps of the aforementioned ultrasound inspection method, such as each of the steps of sound velocity correction including each of the steps of multiline processing described above, and each of the steps of image generation, also constitute an embodiment of the present invention. In addition, a computer-readable recording medium having such a program recorded therein also constitutes an embodiment of the present invention.

What is claimed is:

1. An ultrasound inspection apparatus configured to inspect an inspection object using an ultrasonic beam, the apparatus comprising:
   a probe having a plurality of elements arrayed therein, the probe being configured to transmit the ultrasonic beam, receive an ultrasonic echo reflected by the inspection object, and output an analog element signal corresponding to the received ultrasonic echo;
   a transmitter configured to cause, a plurality of times, the probe to transmit the ultrasonic beam in such a way as to form a predetermined transmission focus using the plurality of elements;
   in accordance with transmission of each ultrasonic beam, a receiver configured to receive the analog element signal output from the plurality of elements and to perform predetermined processing on the analog element signal;
   an A/D converter configured to subject the analog element signal processed by the receiver to A/D conversion to produce a piece of first element data constituted by a digital element signal;
   a sound velocity determiner configured to determine a sound velocity value inside the inspection object; and
   an element data processing section configured to generate a piece of second element data from at least two pieces of the first element data using the sound velocity value inside the inspection object, the piece of second element data corresponding to any of the at least two pieces of first element data;
   an image generator configured to generate an ultrasound image based on the piece of second element data generated in the element data processing section; and
   a processor,
   wherein the element data processing section includes a delay time calculator configured to calculate a delay time of each of the at least two pieces of first element data using the sound velocity value inside the inspection object, and a superimposition processor configured to generate the piece of second element data by superimposing the at least two pieces of first element data based on each calculated delay time and a position of an element of the probe at which receiving has been carried out,
   wherein the element data processing section is performed by the processor,
   wherein the piece of second element data is generated by carrying out delay time correction for one or more pieces of first element data of one or more adjacent element adjacent to element of interest which is selected from the plurality of elements, centering on the piece of first element data of the element of interest, and in addition, phase matching the one or more pieces of first element data of one or more adjacent element in accordance with the difference in element position with the element of interest, and superimposing the two or more pieces of first element data,
   wherein the piece of second element data is obtained based on each of the plurality of elements which is selected as the element of interest,
   wherein the ultrasound image is generated based on the piece of second element data having a high brightness value and selected from the pieces of second element data obtained, and
   wherein the sound velocity determiner obtains an optimum sound velocity value by optimizing the sound velocity value, the sound velocity value being used when the piece of second element data is created from the at least two pieces of first element data in the element data processing section.

2. The ultrasound inspection apparatus according to claim 1, wherein
   the sound velocity determiner includes the element data processing section and is configured to obtain an optimum sound velocity by optimizing the sound velocity value used in a delay time correction calculation for the at least two pieces of first element data in the element data processing section.

3. The ultrasound inspection apparatus according to claim 1, wherein
   the sound velocity determiner is configured to determine a sound velocity value of each of a plurality of regions, the plurality of regions being obtained by the inspection object being divided.

4. The ultrasound inspection apparatus according to claim 1, further comprising an element data storage configured to retain some pieces of the first element data including the at least two pieces of first element data or all pieces of the first element data.

5. The ultrasound inspection apparatus according to claim 4, wherein
   the element data storage retains the at least two pieces of first element data including a piece of reception data, received for each piece of element data, for each reception time in each element, and the at least two pieces of first element data are generated as a result of the transmitter transmitting the ultrasonic beam for every two or more target regions superimposed inside the inspection object and the receiver receiving a signal of the ultrasonic echo generated for every two or more target regions superimposed inside the inspection object by the ultrasonic beam; and wherein the element data processing section generates the piece of second element data from the at least two pieces of first element data, based on a geometrical arrangement of elements when the ultrasonic beam for each piece of element data is transmitted and a geometrical arrangement of the elements of the piece of reception data for each piece of element data.

6. The ultrasound inspection apparatus according to claim 5, wherein the transmitter transmits the ultrasonic beam a plurality of times while changing a central element.

7. The ultrasound inspection apparatus according to claim 1, wherein the element data processing section is configured to create the piece of second element data on one line of an ultrasound image to be generated by the image generator.

8. The ultrasound inspection apparatus according to claim 1, wherein the sound velocity determiner includes:

the element data processing section;

a sound velocity changing section configured to change the sound velocity value of the inspection object used in the delay time calculation in the element data processing section;

the element data processing section configured to create the piece of second element data using the sound velocity value changed by the sound velocity changing section;

a phasing addition section configured to generate a sound ray signal by subjecting the piece of second element data created by the element data processing section to phasing addition using the sound velocity value changed by the sound velocity changing section;

an image generator configured to generate an ultrasound image based on the sound ray signal generated in the phasing addition section;

an image quality index calculator configured to calculate an image quality index for the ultrasound image generated in the image generator;

a determiner configured to determine a set sound velocity when the image quality is best by reading out the image quality indices obtained for the respective sound velocity values calculated in the image quality index calculator and comparing the image quality indices at the respective set sound velocities; and a sound velocity setting section configured to set the optimum sound velocity value in accordance with a determination result for the image quality index made by the determiner;

wherein the sound velocity changing section, the phasing addition section, and the sound velocity setting section are performed by the processor.

9. The ultrasound inspection apparatus according to claim 8, wherein the sound velocity determiner calculates a plurality of the image quality indices corresponding to all of a plurality of the respective sound velocity values changed by the sound velocity changing section, by repeatedly performing an operation in which, each time the sound velocity changing section changes the sound velocity value by a predetermined sound velocity interval from an initial sound velocity value to a final sound velocity value, the element data processing section creates the piece of second element data using the changed sound velocity value, the phasing addition section generates the sound ray signal by subjecting the piece of second element data to phasing addition using the same sound velocity value, the image generator creates the ultrasound image based on the sound ray signal, and the image quality index calculator calculates the image quality index for the ultrasound image, and the determiner determines an optimum image quality index from among the plurality of image quality indices calculated in the image quality index calculator for all of the plurality of respective sound velocity values, and the sound velocity setting section sets a sound velocity value corresponding to the optimum image quality index determined in the determiner as the optimum sound velocity value.

10. The ultrasound inspection apparatus according to claim 1, further comprising a second sound velocity determiner upstream of the sound velocity determiner, the second sound velocity determiner being configured to calculate an optimum sound velocity value using the piece of first element data, the sound velocity determiner being configured to use the sound velocity value calculated by the second sound velocity determiner as an initial value.

11. An ultrasound inspection method for inspecting an inspection object using a probe with a plurality of elements arrayed therein, the probe being configured to transmit an ultrasonic beam, to receive an ultrasonic echo reflected by the inspection object, and to output an analog element signal corresponding to the received ultrasonic echo, the method comprising:

a step of causing, a plurality of times, the probe to transmit an ultrasonic beam in such a way as to form a predetermined transmission focus using the plurality of elements, and causing the plurality of elements to output an analog element signal in accordance with transmission of each ultrasonic beam;

a step of subjecting the analog element signal to A/D conversion to produce a piece of first element data constituted by a digital element signal;

a step of determining, using a sound velocity value in the inspection object, an optimum sound velocity value by optimizing the sound velocity value used when creating, from at least two pieces of the first element data, a piece of second element data corresponding to any of the pieces of first element data;

a step of generating an ultrasound image based on the piece of second element data generated, and a step of calculating a delay time of each of the at least two pieces of first element data using the sound velocity value inside the inspection object, and generating the piece of second element data by superimposing the at least two pieces of first element data based on each calculated delay time and a position of an element of the probe at which receiving has been carried out, wherein the piece of second element data is generated by carrying out delay time correction for one or more pieces of first element data of one or more adjacent element adjacent to element of interest which is selected from the plurality of elements, centering on the piece of first element data of the element of interest, and in addition, phase matching the one or more pieces of first element data of one or more adjacent element in accordance with the difference in element position with the element of interest, and superimposing the two or more pieces of first element data, wherein the piece of second element data is obtained based on each of the plurality of elements which is selected as the element of interest, and wherein the ultrasound image is generated based on the piece of second element data having a high brightness value and selected from the pieces of second element data obtained.

12. The ultrasound inspection method according to claim 11, wherein, in the step of determining the optimum sound velocity value, a plurality of image quality indices corresponding to all of a plurality of the respective changed sound velocity values are calculated by repeatedly performing an operation in which, each time the sound velocity value is changed by a predetermined sound velocity interval from an initial sound velocity value to a final sound velocity value, the piece of second element data is created using the changed sound velocity value, a sound ray signal is generated by subjecting the piece of second element data to phasing addition using the same sound velocity value, the ultrasound image is created based on the generated sound ray signal, and the image quality index for the ultrasound image is calculated by the image quality index calculator, and an optimum image quality index is determined from among the plurality of image quality indices calculated for all of the plurality of respective sound velocity values, and a sound velocity value corresponding to the determined optimum image quality index is set as the optimum sound velocity value.

13. A non-transitory computer-readable recording medium storing a program for causing a computer to execute:

in order to inspect an inspection object by transmitting an ultrasonic beam and receiving an ultrasonic echo reflected by the inspection object, a step of causing, a plurality of times, a probe with a plurality of elements arrayed therein to transmit an ultrasonic beam in such a way as to form a predetermined transmission focus using the plurality of elements, causing the plurality of elements to output an analog element signal in accordance with transmission of each ultrasonic beam, and causing the analog element signal to be subjected to A/D conversion to obtain a plurality of pieces of first element data constituted by digital element signals;

a step of determining, using a sound velocity value inside the inspection object, an optimum sound velocity value by optimizing the sound velocity value used when creating, from at least two pieces of the obtained first element data, a piece of second element data corresponding to any of the pieces of first element data, a step of generating an ultrasound image based on the piece of second element data generated, and a step of calculating a delay time of each of the at least two pieces of first element data using the sound velocity value inside the inspection object, and generating the piece of second element data by superimposing the at least two pieces of first element data based on each calculated delay time and a position of an element of the probe at which receiving has been carried out, wherein the piece of second element data is generated by carrying out delay time correction for one or more pieces of first element data of one or more adjacent element adjacent to element of interest which is selected from the plurality of elements, centering on the piece of first element data of the element of interest, and in addition, phase matching the one or more pieces of first element data of one or more adjacent element in accordance with the difference in element position with the element of interest, and superimposing the two or more pieces of first element data, wherein the piece of second element data is obtained based on each of the plurality of elements which is selected as the element of interest, and wherein the ultrasound image is generated based on the piece of second element data having a high brightness value and selected from the pieces of second element data obtained.

* * * * *